United States Patent
Riedel et al.

(10) Patent No.: US 9,988,268 B2
(45) Date of Patent: Jun. 5, 2018

(54) PREPARATION OF 2,6- AND 2,7-DISUBSTITUTED ANTHRAQUINONE DERIVATIVES

(71) Applicant: BASF SE, Ludwigshafen (DE)

(72) Inventors: Dominic Riedel, Lampertheim (DE); Joaquim Henrique Teles, Waldsee (DE); Thomas Wurm, Heidelberg (DE)

(73) Assignee: BASF SE, Ludwigshafen (DE)

( * ) Notice: Subject to any disclaimer, the term of this patent is extended or adjusted under 35 U.S.C. 154(b) by 0 days. days.

(21) Appl. No.: 15/314,560

(22) PCT Filed: May 28, 2015

(86) PCT No.: PCT/EP2015/061848
§ 371 (c)(1),
(2) Date: Nov. 29, 2016

(87) PCT Pub. No.: WO2015/181297
PCT Pub. Date: Dec. 3, 2015

(65) Prior Publication Data
US 2017/0197830 A1    Jul. 13, 2017

(30) Foreign Application Priority Data
May 30, 2014    (EP) .................................. 14170544

(51) Int. Cl.
*C01B 15/023* (2006.01)
*C07C 50/18* (2006.01)
*C07C 46/00* (2006.01)

(52) U.S. Cl.
CPC ............ *C01B 15/023* (2013.01); *C07C 46/00* (2013.01); *C07C 50/18* (2013.01); *C07B 2200/13* (2013.01)

(58) Field of Classification Search
CPC ....... C07C 46/00; C07C 50/18; C01B 15/023; C07B 2200/13
See application file for complete search history.

(56) References Cited

U.S. PATENT DOCUMENTS

| 4,792,620 A | * | 12/1988 | Paulik ................. B01J 31/0231 560/232 |
| 6,153,169 A | | 11/2000 | Glenneberg et al. |
| 6,355,815 B1 | | 3/2002 | Glenneberg et al. |

FOREIGN PATENT DOCUMENTS

| DE | 1 051 257 B | 2/1959 |
| DE | 43 39 649 A1 | 5/1995 |
| GB | 1 387 511 A | 3/1975 |
| GB | 1 387 512 A1 | 3/1975 |
| WO | WO 99/52819 A1 | 10/1999 |

OTHER PUBLICATIONS

Anonymous, IP.com, Preparation of 2, 6- and 2, 7-disubstituted anthraquinone derivatives, 2014, 12, pp. 1-80.*
Aldrich, Handbook of Fine Chemicals and Laboratory Equipment, 2002, Milwaukee, WI, p. 1016-1017.*
Zaragoza Dorwald, Side Reactions in Organic Synthesis, 2005, Wiley-VCH Verlag GmbH & Co. KGaA, Weinheim, Preface. p. IX.*
International Search Report dated Aug. 3, 2015 in PCT/EP2015/061848.
International Preliminary Report on Patentability and Written Opinion of the International Searching Authority issued Dec. 6, 2016 in PCT/EP2015/061848 filed May 28, 2015.
Gustaaf Goor, et al., "Hydrogen Peroxide" Ullmann's Encyclopedia of Industrial Chemistry, DOI: 10.1002/14356007.a13_443.pub2 vol. 18, 2012, pp. 393-427.

* cited by examiner

*Primary Examiner* — Paul A Zucker
(74) *Attorney, Agent, or Firm* — Oblon, McClelland, Maier & Neustadt, L.L.P.

(57) ABSTRACT

The present invention relates to novel anthraquinone derivatives, 2,6-diisohexylanthracene-9,10-dione and 2,7-diisohexyl-anthracene-9,10-dione, preferably to be used for the preparation of hydrogen peroxide, and to a process for the preparation of these anthraquinone derivatives.

23 Claims, No Drawings

PREPARATION OF 2,6- AND 2,7-DISUBSTITUTED ANTHRAQUINONE DERIVATIVES

The present invention relates to 2,6-diisohexylanthracene-9,10-dione and 2,7-diisohexyl-anthracene-9,10-dione as well as to a composition and a solution comprising 2,6-diisohexylanthracene-9,10-dione and 2,7-diisohexylanthracene-9,10-dione. Further, the present invention relates to a process for the preparation of 2,6-diisohexylanthracene-9,10-dione and 2,7-diisohexylanthracene-9,10-dione as well as to their use in a process for the preparation of hydrogen peroxide. Further, the present invention relates to a process for the preparation of hydrogen peroxide comprising using 2,6-diisohexylanthracene-9,10-dione and 2,7-diisohexylanthracene-9,10-dione.

Anthraquinone compounds are suitable for the preparation of hydrogen peroxide. For example, an anthraquinone process is described in Ullmann's Encyclopedia of Industrial Chemistry, Vol. 18, chapter "Hydrogen Peroxide", DOI: 10.1002/14356007.a13_443.pub2. According to chapter 4 of this document, the following criteria must be fulfilled when applying an anthraquinone derivative to the synthesis of hydrogen peroxide: a) a good solubility of the quinone form and the hydroquinone form in the solvents used in the process, b) good availability, c) good resistance to oxidation, and d) good resistance to hydrogenation of the aromatic rings in the anthraquinone molecule.

GB 1 387 511 A1 and GB 1 387 512 A1 are directed to a process for the preparation of hydrogen peroxide by use of alkylanthraquinones, wherein the solubility of the dialkylanthraquinones is in the range of from 0.64 mol/l to 0.70 mol/l and 0.65 mol/l to 1.02 mol/l, respectively. Further, GB 1 387 511 A1 and GB 1 387 512 A1 describe general processes for the preparation of the dialkylanthraquinones by condensing a 4-alkyl substituted phthalic acid anhydride and an alkylbenzene in the presence of a catalyst or by an alkylation reaction followed by oxidation of the obtained anthracene. According to the examples of GB 1 387 511 A1 and GB 1 387 512 A1 only one specific compound, 2-methyl-amylanthraquinone, is used in a process for the preparation of hydrogen peroxide. However, the preparation of 2-methyl-amylanthraquinone is expensive and therefore, highly disadvantageous for industrial-scale processes.

DE 43 39 649 A1 is directed to a process for the preparation of hydrogen peroxide wherein alkylanthraquinones are employed. According to this document, a mixture of 1,3-diethylanthraquinone, 2,3-diethylanthraquinone, 1,4-diethylanthraquinone, 1,2,3-triethylanthraquinone and 2-ethylanthraquinone is used for increasing the solubility of the anthraquinone derivatives in the solvent used in the process for the preparation of hydrogen peroxide.

DE 1 051 257 B is directed to a process for the preparation of hydrogen peroxide via an anthraquinone process, wherein anthraquinone derivatives having two or three alkyl residues are used. According to DE 1 051 257 B, it is preferred to use a mixture of isomers of the anthraquinone derivatives.

In the prior art several anthraquinone derivatives are disclosed for use in a process for the preparation of the hydrogen peroxide. However, the disclosed anthraquinone derivatives are either expansive to prepare and/or not sufficiently soluble in the solvents which are commonly used for the preparation of hydrogen peroxide and/or not sufficiently stable towards hydrogenation of the aromatic ring systems, leading to products that are not active with respect to hydrogen peroxide synthesis anymore.

It was an object of the present invention to provide a novel anthraquinone derivative which can be prepared by an efficient and cost effective process, in particular a novel anthraquinone derivative which has a better suitability than known anthraquinone derivatives when used in a process for the preparation of hydrogen peroxide, including a higher stability towards over-hydrogenation reactions.

Surprisingly, it was found that the novel compounds 2,6-diisohexylanthracene-9,10-dione and 2,7-diisohexyl-anthracene-9,10-dione exhibit a high solubility in solvents suitable for use in a process for the preparation of hydrogen peroxide and at the same time, are available by a sustainable, atom efficient as well as cost effective process.

Therefore, the present invention relates to a compound of formula (Ia)

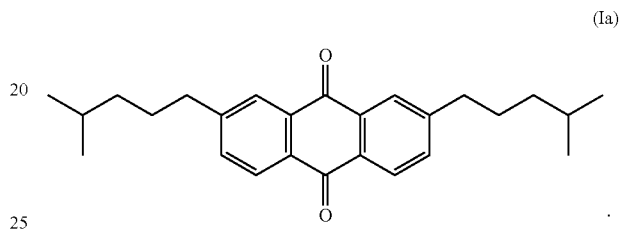

(Ia)

Further, the present invention related to a compound of formula (Ib)

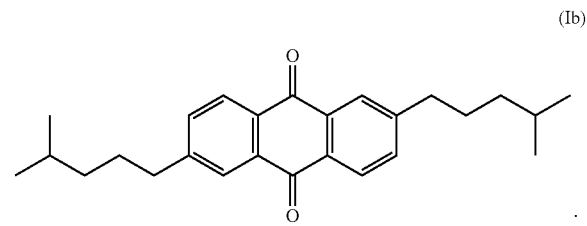 [SMILES: CC(C)CCCc1ccc2c(c1)C(=O)c1ccc(CCCC(C)C)cc1C2=O]

(Ib)

Further, the present invention relates to a composition comprising a compound of formula (Ia)

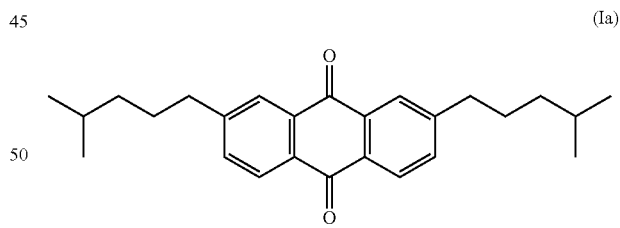

(Ia)

and a compound of formula (Ib)

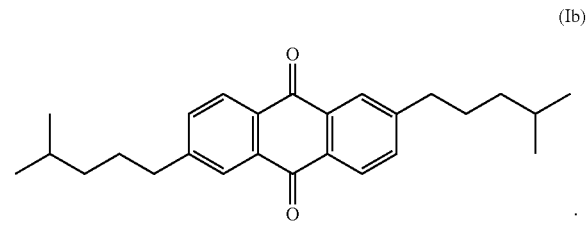 [SMILES: CC(C)CCCc1ccc2c(c1)C(=O)c1ccc(CCCC(C)C)cc1C2=O]

(Ib)

Composition

Generally, there are no specific restrictions regarding the amount of the compounds of formula (Ia) and formula (Ib) in the composition comprising the compounds of formula (Ia) and (Ib). According to the present invention, it is preferred that at least 90 weight-%, more preferably at least 92 weight-%, more preferably at least 94 weight-%, more preferably at least 96 weight-%, such as at least 99 weight-%, of the composition consist of the compounds of formula (Ia) and formula (Ib).

As far as the amounts of the compound of formula (Ia) and of formula (Ib) in the composition comprising the compounds of formula (Ia) and (Ib) are concerned, no specific restrictions exist. Preferably, in the composition comprising the compounds of formula (Ia) and of formula (Ib), the molar ratio of the compound of formula (Ia) relative to the compound of formula (Ib) is in the range of from 0.2:1 to 5:1, preferably from 0.3:1 to 3:1, more preferably from 0.5:1 to 2:1, more preferably from 0.8:1 to 1.2:1. Preferred ranges are, for example, from 0.8:1 to 1.0:1 or from 0.9:1 to 1.1:1 or from 1.0:1 to 1.2:1.

Therefore, the present invention preferably relates to a composition comprising the compounds of formula (Ia) and (Ib) wherein at least 90 weight-%, of the composition consist of the compounds of formula (Ia) and formula (Ib) and wherein the molar ratio of the compound of formula (Ia) relative to the compound of formula (Ib) is in the range of from 0.5:1 to 2:1. More preferably, the present invention relates to a composition comprising the compounds of formula (Ia) and (Ib) wherein at least 94 weight-%, of the composition consist of the compounds of formula (Ia) and formula (Ib) and wherein the molar ratio of the compound of formula (Ia) relative to the compound of formula (Ib) is in the range of from 0.8:1 to 1.2:1. More preferably, the present invention relates to a composition comprising the compounds of formula (Ia) and (Ib) wherein at least 96 weight-%, of the composition consist of the compounds of formula (Ia) and formula (Ib) and wherein the molar ratio of the compound of formula (Ia) relative to the compound of formula (Ib) is in the range of from 0.8:1 to 1.2:1.

It was surprisingly found that the compounds of the present invention exhibit a high solubility in a solvent mixture of which at least 99.9 weight-% consist of ortho-xylene and diisobutyl carbinol. Preferably, the composition according to the present invention has a solubility of at least 1.0 mol/l, more preferably of at least 1.4 mol/l, more preferably in the range of from 1.4 to 1.8 mol/l, in a solvent mixture of which at least 99.9 weight-% consist of ortho-xylene and diisobutyl carbinol with a molar ratio of the ortho-xylene relative to the diisobutyl carbinol in the range of from 0.99:1 to 1.01:1, wherein said solubility refers to the molar amount of the compound of formula (Ia) plus the molar amount of the compound of formula (Ib) dissolved in 1 l of the solvent mixture at a temperature in the range of from 20 to 23° C. and at a pressure in the range of from 0.9 to 1.1 bar.

Preferably, at least 90 weight-%, more preferably at least 92 weight-%, more preferably at least 94 weight-% of the compound of formula (Ia) and at least 96 weight-%, preferably at least 98 weight-%, more preferably at least 99 weight-% of the compound of formula (Ib) are present in solid form, preferably in solid crystalline form.

As far as conceivable uses, in particular the use for the preparation of hydrogen peroxide are concerned, it is preferred that the composition comprising a compound of formula (Ia) and a compound of formula (Ib) is at least partially, preferably completely dissolved in a solvent.

As far as the solvent used to dissolve the composition comprising a compound of formula (Ia) and a compound of formula (Ib) is concerned, no specific restrictions exist, provided that the composition comprising a compound of formula (Ia) and a compound of formula (Ib) is at least partially, preferably completely dissolvable in the solvent. Preferably, the solvent is selected from the group consisting of benzene, monoalkylated benzene, for example toluene and tert-butylbenzene, polyalkylated benzene, for example xylene, methylnaphthalene, alkyl phosphates, alkylcyclohexanol esters, N,N-dialkyl carbonamides, N-alkyl carbonamides, N-aryl carbonamides, N,N-dialkyl carbamates, tetraalkyl ureas, cycloalkyl ureas, phenylalkyl ureas, N-alkyl-2-pyrrolidones, N-alkyl caprolactams, alcohols having from 1 to 12 carbon atoms and a mixture of two or more thereof, more preferably selected from the group consisting of trimethylbenzene, tetramethylbenzene, alkyl phosphates, nonyl alcohols, N,N-dialkyl carbonamides, N,N-dialkyl carbamates, N-alkyl carbonamides, tetraalkyl ureas, cycloalkyl ureas, and a mixture of two or more thereof.

If a mixture of two or more of these solvents is used, it is preferred, for example, to use a mixture of polyalkylated benzene and alkyl phosphates or a mixture of polyalkylated benzene and tetraalkyl ureas or a mixture of methylnaphthalene and nonyl alcohols or a mixture of trimethylbenzenes and alkyl cyclohexanol esters Thus, it is particularly preferred that the composition comprising a compound of formula (Ia) and a compound of formula (Ib) is at least partially, preferably completely, dissolved in a solvent, wherein the solvent is preferably selected from the group consisting of benzene, monoalkylated benzene, preferably toluene or tert-butylbenzene, polyalkylated benzene, preferably xylene, methylnaphthalene, alkyl phosphates, alkylcyclohexanol esters, N,N-dialkyl carbonamides, N-alkyl carbonamides, N-aryl carbonamides, N,N-dialkyl carbamates, tetraalkyl ureas, cycloalkyl ureas, phenylalkyl ureas, N-alkyl-2-pyrrolidones, N-alkyl caprolactams, alcohols having from 1 to 12 carbon atoms, and a mixture of two or more thereof, more preferably selected from the group consisting of trimethylbenzene, tetramethylbenzene, alkyl phosphates, nonyl alcohols, N,N-dialkyl carbonamides, N,N-dialkyl carbamates, N-alkyl carbonamides, tetraalkyl ureas, cycloalkyl ureas, and a mixture of two or more thereof.

Solution

Further, the present invention relates to a solution comprising a compound of formula (Ia) and a solvent as well as to a solution comprising a compound of formula (Ib) and a solvent. Also, the present invention relates to a solution comprising a compound of formula (Ia) and a compound of formula (Ib) and further comprising a solvent.

Concerning the solution comprising a compound of formula (Ia) and a compound of formula (Ib) and further comprising a solvent, no specific restrictions exist regarding the molar ratio of the compound of formula (Ia) relative to the compound of formula (Ib). Preferably, the molar ratio of the compound of formula (Ia) relative to the compound of formula (Ib) in the solution comprising a compound of formula (Ia) and a compound of formula (Ib) and further comprising a solvent is in the range of from 0.2:1 to 5:1, preferably from 0.3:1 to 3:1, more preferably from 0.4:1 to 2.5:1, more preferably from 0.5:1 to 2:1, more preferably from 0.6:1 to 1.8:1, more preferably form 0.8:1 to 1.4:1, more preferably from 0.8:1 to 1.2:1. Preferred ranges are, for example, from 0.8:1 to 1.0:1 or from 0.9:1 to 1.1:1 or from 1.0:1 to 1.2:1.

As far as the solvent comprised in the solution comprising a compound of formula (Ia) and a compound of formula (Ib) is concerned, no specific restrictions exist; in particular, polar solvents as well as non-polar solvents are conceivable. Preferably, the solvent is selected from the group consisting of benzene, monoalkylated benzene, preferably toluene or tert-butylbenzene, polyalkylated benzene, preferably xylene, methylnaphthalene, alkyl phosphates, alkylcyclohexanol esters, N,N-dialkyl carbonamides, N-alkyl carbonamides, N-aryl carbonamides, N,N-dialkyl carbamates, tetraalkyl ureas, cycloalkyl ureas, phenylalkyl ureas, N-alkyl-2-pyrrolidones, N-alkyl caprolactams, alcohols having from 1 to 12 carbon atoms and a mixture of two or more thereof, more preferably selected from the group consisting of trimethylbenzene, tetramethylbenzene alkyl phosphates, nonyl alcohols, N,N-dialkyl carbonamides, N,N-dialkyl carbamates, N-alkyl carbonamides, tetraalkyl ureas, cycloalkyl ureas, and a mixture of two or more thereof.

If a mixture of two or more of these solvents is used, it is preferred to use a mixture of polyalkylated benzene and alkyl phosphates or a mixture of polyalkylated benzene and tetraalkyl ureas or a mixture of methylnaphthalene and nonyl alcohols or a mixture of trimethylbenzenes and alkyl cyclohexanol esters.

Concerning the concentration of the compound of formula (Ia) and formula (Ib) in the solution comprising the compound of formula (Ia) and a compound of formula (Ib) and further comprising a solvent, the concentration of the sum of the compounds of formula (Ia) and formula (Ib) is preferably in the range of from 0.2 to 2.4 mol/l, more preferably in the range of from 0.4 to 2.3 mol/l, more preferably in the range of from 0.6 to 2.2 mol/l, more preferably in the range of from 0.8 to 2.0 mol/l, more preferably in the range of from 1.0 to 1.8 mol/l.

Thus, the present invention relates to a solution comprising a compound of formula (Ia)

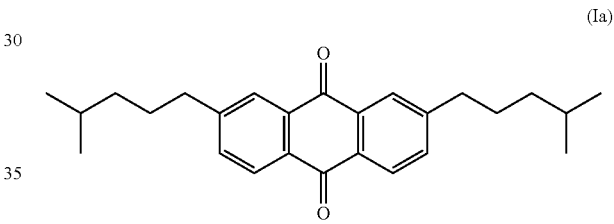
(Ia)

and/or, preferably and, a compound of formula (Ib)

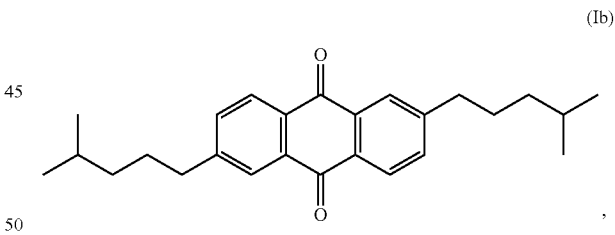
(Ib)
, and further comprising a solvent, wherein the molar ratio of the compound of formula (Ia) relative to the compound of formula (Ib) is preferably in the range of from 0.2:1 to 5:1, preferably from 0.3:1 to 3:1, more preferably from 0.5:1 to 2:1, more preferably from 0.8:1 to 1.2:1, wherein the solvent is preferably selected from the group consisting of benzene, monoalkylated benzene, preferably toluene or tert-butylbenzene, polyalkylated benzene, preferably xylene, methylnaphthalene, alkyl phosphates, alkylcyclohexanol esters, N,N-dialkyl carbonamides, N-alkyl carbonamides, N-aryl carbonamides, N,N-dialkyl carbamates, tetraalkyl ureas, cycloalkyl ureas, phenylalkyl ureas, N-alkyl-2-pyrrolidones, N-alkyl caprolactams, alcohols having from 1 to 12 carbon atoms and a mixture of two or more thereof, more preferably selected from the group consisting of trimethylbenzene, tetramethylbenzene, alkyl phosphates, nonyl alcohols, N,N-dialkyl carbonamides, N,N-dialkyl carbamates, N-alkyl carbonamides, tetraalkyl ureas, cycloalkyl ureas, and a mixture of two or more thereof, and wherein the concentration of the sum of the compounds of formula (Ia) and formula (Ib) is preferably in the range of from 0.6 to 2.2 mol/l, more preferably in the range of from 0.8 to 2.0 mol/l, more preferably in the range of from 1.0 to 1.8 mol/l.

Process

Further, the present invention relates to a process for the preparation of a composition comprising a compound of formula (Ia)

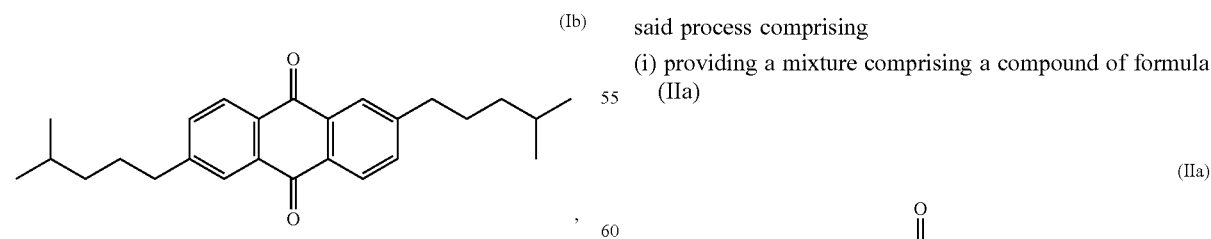
(Ia)

and/or, preferably and, a compound of formula (Ib)

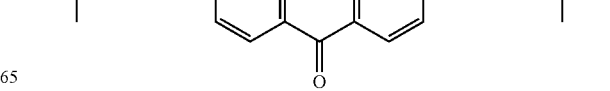
(Ib)
, said process comprising
(i) providing a mixture comprising a compound of formula (IIa)

(IIa)

and/or, preferably and, a compound of formula (IIb)

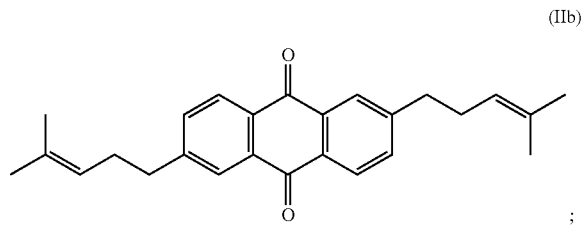 [SMILES: CC(C)=CCCc1ccc2c(c1)C(=O)c1ccc(CCC=C(C)C)cc1C2=O]
(IIb)

(ii) subjecting the mixture provided in (i) to a hydrogenation reaction, preferably in the presence of a hydrogenation catalyst.

Thus, the present invention relates to a process for the preparation of a composition comprising a compound of formula (Ia) as well as to a process for the preparation of a composition comprising a compound of formula (Ib). Further, the present invention relates to a process for the preparation of a composition comprising a compound of formula (Ia) and a compound of formula (Ib).

Step (i)

According to the present invention, in the process for the preparation of a composition comprising a compound of formula (Ia) or comprising a compound of formula (Ib), or comprising a compound of formula (Ia) and a compound of formula (Ib), preferably comprising a compound of formula (Ia) and a compound of formula (Ib), (i) preferably comprises (a) providing a compound of formula (III)

(III)

(b) reacting, preferably in a solvent, the compound of formula (III) provided in (a) with a compound of formula (IV)

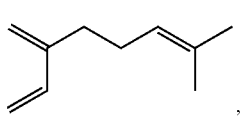
(IV)

obtaining a mixture comprising a compound of formula (Va)

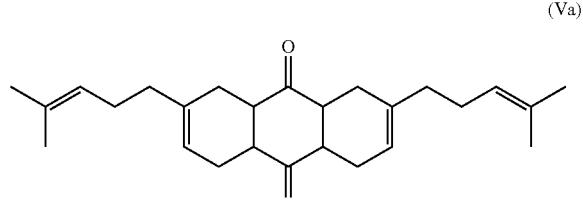
(Va)

and/or, preferably and, a compound of formula (Vb)

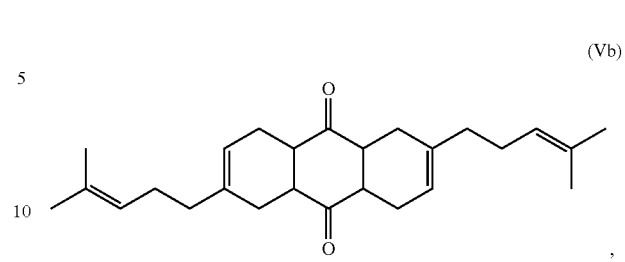
(Vb)

(c) subjecting the mixture obtained in (b) to an oxidation reaction, preferably in the presence of an oxygen containing gas, preferably selected from the consisting of oxygen, air, and lean air, and preferably in the presence of an inorganic base, preferably selected from the group consisting of potassium hydroxide, sodium hydroxide, and a combination thereof, obtaining a mixture comprising the compound of formula (IIa) and/or, preferably and, the compound of formula (IIb).

The term "providing" as used in this context of the present invention relates to the respective process after which the respective compound which is provided is available for further reaction in a subsequent step.

Generally, there are no specific restrictions how the compound of formula (III) is provided in (a). For example, it is conceivable to purchase a suitable, commercially available compound of formula (III). Further, for example, any conceivable process for synthesizing such a compound can be employed for providing the compound of formula (III). Preferably, the compound of formula (III) is provided in (a) by a process comprising providing a compound of formula (VI)

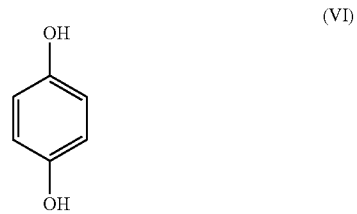
(VI)

which is, more preferably, subjected to a dehydrogenation reaction.

Therefore, preferably, in (a), the compound of formula (III) is provided by a method comprising (a.1) providing a compound of formula (VI)

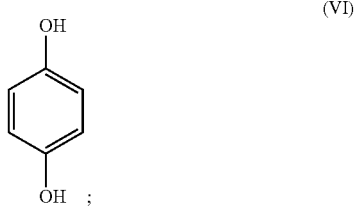
(VI)

(a.2) subjecting the compound of formula (VI) provided in (a.1), preferably in an organic solvent, to a dehydrogenation reaction, preferably in the presence of a dehydrogenation catalyst.

Generally, there are no specific restrictions how the compound of formula (VI) is provided in (a.1). For example, it may be conceivable to purchase a suitable, commercially available compound of formula (VI). Further, for example, any conceivable process for synthesizing such a compound can be employed for providing the compound of formula (VI). After providing the compound of formula (VI) in (a.1), the compound of formula (VI) is preferably subjected to a dehydrogenation reaction.

Generally, the dehydrogenation reaction according to (a.2) may be carried out in the absence of a dehydrogenation catalyst, for example by oxidizing the compound of formula (VI) with oxygen in the absence of a dehydrogenation catalyst.

Preferably, the dehydrogenation reaction according to (a.2) is carried out in the presence of a dehydrogenation catalyst, wherein no specific restrictions exist regarding the nature of the catalyst provided that the dehydrogenation reaction takes place. Preferably, the dehydrogenation reaction according to (a.2) is carried out in the presence of a dehydrogenation catalyst, wherein the dehydrogenation catalyst comprises one or more elements selected from the group consisting of the transition, wherein the dehydrogenation catalyst more preferably comprises copper and at least one additional element selected from the group consisting of lithium, zinc, zirconium, aluminum, and a combination of two or more thereof, wherein the dehydrogenation catalyst more preferably comprises a combination of copper and lithium or a combination of copper, zinc, zirconium and aluminum. More preferably, the dehydrogenation catalyst comprises, more preferably consists of, a combination of lithium chloride and copper(II) chloride, or a combination of copper(II) oxide, zinc(II) oxide, zirconium(IV) oxide and aluminum oxide.

Generally, there are no specific restrictions how the catalyst is employed in the reaction according to (a.2) provided that the reaction according to (a.2) tale place. Preferably, the catalyst is employed suspended or dissolved in a suitable solvent or solvent mixture, preferably comprising water. If the dehydrogenation catalyst comprises, preferably consists of, a combination of lithium chloride and copper(II) chloride, it is particularly preferred that the dehydrogenation catalyst is at least partially, more preferably completely, dissolved in water.

As far as the organic solvent used in (a.2) is concerned, no specific restrictions exist, provided that the dehydrogenation according to (a.2) takes place. Preferably, the organic solvent according to (a.2) is selected from the group consisting of benzene, monoalkylated benzene, preferably toluene or tert-butylbenzene, polyalkylated benzene, preferably xylene, methylnaphthalene, alkyl phosphates, alkylcyclohexanol esters, N,N-dialkyl carbonamides, N-alkyl carbonamides, N-aryl carbonamides, N,N-dialkyl carbamates, tetraalkyl ureas, cycloalkyl ureas, phenylalkyl ureas, N-alkyl-2-pyrrolidones, N-alkyl caprolactams, alcohols having from 1 to 12 carbon atoms, and a mixture of two or more thereof, preferably selected from the group consisting of trimethylbenzene, tetramethylbenzene, alkyl phosphates, nonyl alcohols, N,N-dialkyl carbonamides, N,N-dialkyl carbamates, N-alkyl carbonamides, tetraalkyl ureas, cycloalkyl ureas, and a mixture of two or more thereof.

If a mixture of two or more of these organic solvents is used, it is preferred to use a mixture of polyalkylated benzene and alkyl phosphates or a mixture of polyalkylated benzene and tetraalkyl ureas or a mixture of methylnaphthalene and nonyl alcohols or a mixture of trimethylbenzenes and alky cyclohexanol esters.

Concerning the temperature at which the dehydrogenation reaction according to (a.2) is carried out, no specific restrictions exist provided that the dehydrogenation reaction takes place.

According to the present invention, it is preferred that the temperature at the beginning of the hydrogenation reaction according to (a.2) is in the range of from 10 to 120° C., preferably from 20 to 90° C., more preferably from 30 to 70° C., such as from 30 to 60° C. or from 40 to 65° C. or from 50 to 70° C.

As far as the solvent used in (b) is concerned, no specific restrictions exist, provided that the compound of formula (III) provided in (a) reacts with a compound of formula (IV). Preferably, the reaction according to (b) is carried out in a solvent, preferably in an organic solvent, more preferably selected from the group consisting of benzene, monoalkylated benzene, preferably toluene or tert-butylbenzene, polyalkylated benzene, preferably xylene, methylnaphthalene, alkyl phosphates, alkylcyclohexanol esters, N,N-dialkyl carbonamides, N-alkyl carbonamides, N-aryl carbonamides, N,N-dialkyl carbamates, tetraalkyl ureas, cycloalkyl ureas, phenylalkyl ureas, N-alkyl-2-pyrrolidones, N-alkyl caprolactams, alcohols having from 1 to 12 carbon atoms, and a mixture of two or more thereof, more preferably selected from the group consisting of trimethylbenzene, tetramethylbenzene, alkyl phosphates, nonyl alcohols, N,N-dialkyl carbonamides, N,N-dialkyl carbamates, N-alkyl carbonamides, tetraalkyl ureas, cycloalkyl ureas, and a mixture of two or more thereof.

If a mixture of two or more of these organic solvents is used, it is preferred to use a mixture of polyalkylated benzene and alkyl phosphates or a mixture of polyalkylated benzene and tetraalkyl ureas or a mixture of methylnaphthalene and nonyl alcohols or a mixture of trimethylbenzenes and alky cyclohexanol esters.

As far as the amounts of the compound of formula (III) and of the compound of formula (IV) at the beginning of the reaction according to (b) are concerned, no specific restrictions exist provided that a compound of formula (Va) and/or a compound of formula (Vb) are obtained. Preferably, at the beginning of the reaction according to (b), the molar ratio of the compound of formula (IV) relative to the compound of formula (III) is in the range of from 1:1 to 10:1, preferably from 1:1 to 5:1, more preferably from 1:1 to 3:1, more preferably from 1:1 to 2:1.

Furthermore, the reaction according to (b) may be carried out without the use of the above mentioned solvents. Thus, according to the present invention, it is conceivable to carry out the reaction according to (b) by use of an excess of compound of (IV), which in this case acts as solvent.

As far as the temperature at which the reaction according to (b) is carried out is concerned, no specific restrictions exist, provided that a compound of formula (Va) and/or a compound of formula (Vb) is/are obtained. Preferably, the reaction according to (b) is carried out at a temperature in the range of from 50 to 250° C., preferably from 60 to 200° C., more preferably from 70 to 150° C., more preferably from 75° C. to 100° C.

No specific restrictions exist concerning the period of time during which the reaction according to (b) is carried out, provided that a compound of formula (Va) and/or a compound of formula (Vb) is/are obtained. The reaction according to (b) is preferably carried out for a period of time in the range of from 5 to 260 h, more preferably from 10 to 192 h, more preferably from 15 to 120 h, more preferably from 15 to 96 h, more preferably from 18 to 72 h, more preferably from 20 to 48 h, more preferably from 22 to 30 h.

Further, the mixture obtained in (b) may contain a dimer of the compound of formula (IV), wherein the dimer may be formed by a Diels-Alder reaction of two molecules of the formula (IV). Preferably, the dimer of the compound of formula (IV) is separated from the mixture obtained in (b), wherein all methods of separating the dimer of the compound of formula (IV) are conceivable. The separated dimer of the compound of formula (IV) is preferably subjected to a retro-Diels-Alder reaction, wherein a compound of formula (IV) is obtained. The compound (IV) obtained from the retro-Diels-Alder reaction may be used, for example, as compound (IV) in (b). Therefore, according to an embodiment of the present invention, the mixture obtained in (b) comprises a dimer of the compound of formula (IV). In this case, it is preferred that the process for providing a mixture comprising a compound of formula (IIa) and/or, preferably and, a compound of formula (IIb), further comprises (b.1) separating the dimer of compound (IV) from the mixture obtained in (b);

(b.2) subjecting the separated dimer of the compound of formula (IV) to a retro-Diels-Alder reaction, obtaining a compound of formula (IV);

wherein the compound of formula (IV) is subjected to the reaction according to (b).

Optionally, the process for providing a mixture comprising a compound of formula (IIa) and/or, preferably and, a compound of formula (IIb), further comprises, after (b) and prior to (c), (b') separating the compounds of formula (Va) and/or, preferably and, formula (Vb) from the mixture obtained in (b), obtaining a mixture comprising the compounds of formula (Va) and/or, preferably and, formula (Vb), wherein preferably at least 90 weight-%, more preferably at least 92 weight-%, more preferably at least 94 weight-%, more preferably at least 96 weight-%, such as at least 98 weight-% or at least 99 weight-%, of the obtained mixture consist of the compounds of formula (Va) and (Vb).

As regards the separation according to (b'), all methods of separating the compounds of formula (Va) and/or, preferably and, formula (Vb) from the mixture obtained in (b) are conceivable. These methods include, but are not restricted to, crystallization, filtration, centrifugation, extraction and distillation methods. A combination of two or more of these methods can be applied. Preferably, the compounds of formula (Va) and/or, preferably and, formula (Vb) are separated from the mixture obtained in (b) by filtration.

According to the present invention it is preferred that prior to (c), the compounds of formula (Va) and/or, preferably and, formula (Vb) are not separated from the mixture obtained in (b). Thus, it is preferred that the sequence of steps (a) to (b) is carried out as a one-pot process.

The mixture obtained in (b) is subjected to an oxidation reaction, preferably in the presence of an oxygen containing gas. As far as the oxygen containing gas used in (c) is concerned, no specific restrictions exist, provided that a mixture comprising the compound of formula (IIa) and/or, preferably and, the compound of formula (IIb) is obtained. Preferably, the oxygen containing gas is selected from the group consisting of oxygen, air, lean air, and a mixture of two or more thereof.

As far as the solvent used in the oxidation reaction according to (c) is concerned, no specific restrictions exist. Polar solvents as well as non-polar solvents may be used. Preferably, the oxidation reaction according to (c) is carried out in a solvent, preferably an organic solvent, wherein the solvent is more preferably selected from the group consisting of benzene, monoalkylated benzene, preferably toluene or tert-butylbenzene, polyalkylated benzene, preferably xylene, methylnaphthalene, alkyl phosphates, alkylcyclohexanol esters, N,N-dialkyl carbonamides, N-alkyl carbonamides, N-aryl carbonamides, N,N-dialkyl carbamates, tetraalkyl ureas, cycloalkyl ureas, phenylalkyl ureas, N-alkyl-2-pyrrolidones, N-alkyl caprolactams, alcohols having from 1 to 12 carbon atoms, and a mixture of two or more thereof, more preferably selected from the group consisting of trimethylbenzene, tetramethylbenzene, alkyl phosphates, nonyl alcohols, N,N-dialkyl carbonamides, N,N-dialkyl carbamates, N-alkyl carbonamides, tetraalkyl ureas, cycloalkyl ureas, and a mixture of two or more thereof.

If a mixture of two or more of these solvents is used, it is preferred to use a mixture of polyalkylated benzene and alkyl phosphates or a mixture of polyalkylated benzene and tetraalkyl ureas or a mixture of methylnaphthalene and nonyl alcohols or a mixture of trimethylbenzenes and alky cyclohexanol esters.

Further, it is preferred to carry out the oxidation reaction according to (c) in the presence of an inorganic base. Concerning the nature of the inorganic base, no specific restrictions exist provided that a mixture comprising the compound of formula (IIa) and/or, preferably and, the compound of formula (IIb) is obtained. Preferred inorganic bases include, but are not restricted to, alkali metal bases and alkaline earth metal bases, preferably hydroxides, more preferably alkali metal bases, more preferably alkali metal hydroxides, more preferably potassium and/or sodium hydroxides. Thus, the oxidation reaction according to (c) is preferably carried out in the presence of an inorganic base, preferably selected from the croup consisting potassium hydroxide, sodium hydroxide, and a combination thereof. According to the present invention, it is particularly preferred that the inorganic base is potassium hydroxide.

As far as the temperature at which the oxidation reaction according to (c) is carried out are concerned, no specific restrictions exist provided that a mixture comprising the compound of formula (IIa) and/or, preferably and, the compound of formula (IIb) is obtained. Preferably, the temperature at the beginning of the oxidation reaction according (c) is the range of from 30 to 150° C., preferably from 40 to 100° C., more preferably from 50 to 90° C., more preferably from 55 to 80° C.

As far as the period of time during which the oxidation reaction according to (c) is carried out is concerned, no specific restrictions exist provided that a mixture comprising the compound of formula (IIa) and/or, preferably and, the compound of formula (IIb) is obtained. Preferably, the oxidation reaction according to (c) is carried out for a period of time in the range of from 0.2 to 24 h, preferably from 0.5 to 12 h, more preferably from 1 to 8 h.

Optionally, the process for providing a mixture comprising a compound of formula (IIa) and/or, preferably and, a compound of formula (IIb), further comprises, after (c) and prior to (ii), (c') separating the compounds of formula (IIa) and/or, preferably and, formula (IIb) from the mixture obtained in (c), obtaining a mixture comprising the compounds of formula (IIa) and/or, preferably and, formula (IIb), wherein preferably at least 90 weight-%, more preferably at least 92 weight-%, more preferably at least 94 weight-%, more preferably at least 96 weight-%, such as at least 98 weight-% or at least 99 weight-%, of the obtained mixture consist of the compounds of formula (IIa) and (IIb), wherein said separating preferably comprises crystallizing, more preferably comprises extracting and crystallizing, the compounds of formula (IIa) and/or, preferably and, formula (IIb).

As regards the separation according to (c'), all methods of separating the compounds of formula (IIa) and/or, preferably and, formula (IIb) from the mixture obtained in (c) are conceivable. These methods include filtration, centrifugation, and distillation methods. A combination of two or more of these methods can be applied. Preferably, the compounds of formula (IIa) and/or, preferably and, formula (IIb) are separated from the mixture obtained in (c) by filtration.

According to the present invention, it is particularly preferred that after (c) and prior to (ii) the compounds of formula (IIa) and/or, preferably and, formula (IIb) are not separated from the mixture obtained in (c). Thus, preferably, the sequence of steps (a) to (c) is carried out as a one pot process. Consequently, the present invention also relates to the process as described above, comprising (i) providing a mixture comprising a compound of formula (IIa)

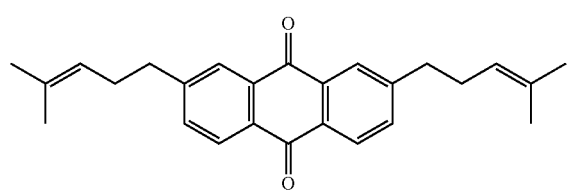

and/or, preferably and, a compound of formula (IIb)

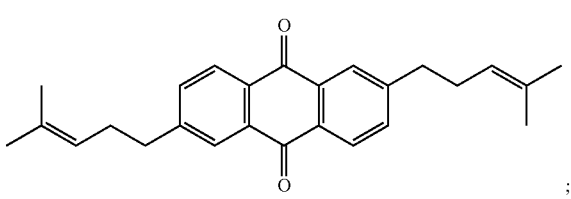

wherein (i) comprises (a) providing a compound of formula (III)

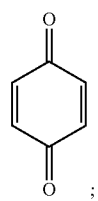

(b) reacting, preferably in a solvent, the compound of formula (III) provided in (a) with a compound of formula (IV)

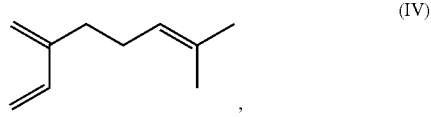

obtaining a mixture comprising a compound of formula (Va)

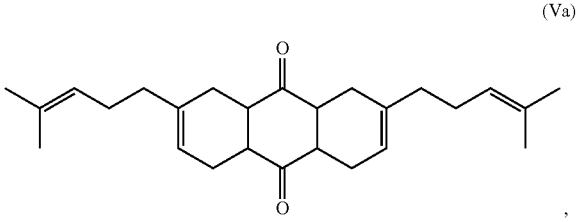 [SMILES: CC(C)=CCCC1=CCC2C(=O)C3CC=C(CCC=C(C)C)CC3C(=O)C2C1]

and/or, preferably and, a compound of formula (Vb)

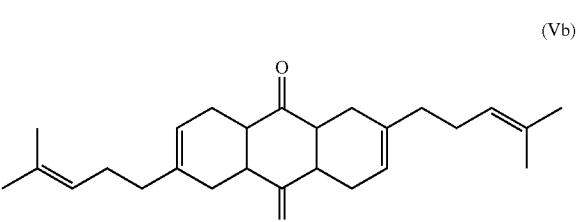

(c) subjecting the mixture obtained in (b) to an oxidation reaction, preferably in the presence of an oxygen containing gas, preferably selected from the consisting of oxygen, air, and lean air, and preferably in the presence of an inorganic base, preferably selected from the group consisting of potassium hydroxide, sodium hydroxide, and a combination thereof, obtaining a mixture comprising the compound of formula (IIa) and/or, preferably and, the compound of formula (IIb);

(ii) subjecting the mixture provided in (i) to a hydrogenation reaction, preferably in the presence of a hydrogenation catalyst, wherein after (c) and prior to (ii) the compounds of formula (IIa) and/or, preferably and, formula (IIb) are not separated from the mixture obtained in (c).

According to the present invention, it is particularly preferred to carry out the oxidation reaction according to (c) in the presence of an inorganic base, wherein after (c) and prior to (ii) the compounds of formula (IIa) and/or, preferably and, formula (IIb) are not separated from the mixture obtained in (c). In this case it is preferred that, after (c) and prior to (ii), the inorganic base is at least partially, preferably completely separated in a step (c") from the mixture obtained in (c), wherein a mixture is obtained being depleted in the inorganic base and comprising the compounds of formula (IIa) and/or, preferably and, formula (IIb).

As regards the separation according to (c"), all methods of separating the inorganic base from the mixture obtained in (c) are conceivable. Preferably, the separation comprises extracting the inorganic base, wherein the inorganic base is preferably extracted with an aqueous solution, more preferably with water.

Thus, it is particularly preferred that after (c) and prior to (ii), the compounds of formula (IIa) and/or, preferably and, formula (II) are not separated from the mixture obtained in (c), wherein, if the oxidation reaction according to (c) is carried out in the presence of an inorganic base, the process after (c) and prior to (ii) preferably further comprises (c'') separating the inorganic base at least partially, preferably completely, from the mixture obtained in (c), obtaining a mixture being depleted in the inorganic base and comprising the compounds of formula (IIa) and/or, preferably and, formula (IIb), wherein said separating preferably comprises extracting the inorganic base, preferably with water.

Step (ii)

As far as the solvent used in the hydrogenation reaction according to (ii), no specific restrictions exist, provided that the hydrogenation reaction according to (ii) takes place. Preferably, the hydrogenation reaction according to (ii) is carried out in a solvent, preferably an organic solvent, wherein the solvent is more preferably selected from the group consisting of benzene, monoalkylated benzene, preferably toluene or tert-butylbenzene, polyalkylated benzene, preferably xylene, methylnaphthalene, alkyl phosphates, alkylcyclohexanol esters, N,N-dialkyl carbonamides, N-alkyl carbonamides, N-aryl carbonamides, N,N-dialkyl carbamates, tetraalkyl ureas, cycloalkyl ureas, phenylalkyl ureas, N-alkyl-2-pyrrolidones, N-alkyl caprolactams, alcohols having from 1 to 12 carbon atoms, and a mixture of two or more thereof, more preferably selected from the group consisting of trimethylbenzene, tetramethylbenzene, alkyl phosphates, nonyl alcohols, N,N-dialkyl carbonamides, N,N-dialkyl carbamates, N-alkyl carbonamides, tetraalkyl ureas, cycloalkyl ureas, and a mixture of two or more thereof.

If a mixture of two or more of these organic solvents is used, it is preferred to use a mixture of polyalkylated benzene and alkyl phosphates or a mixture of polyalkylated benzene and tetraalkyl ureas or a mixture of methylnaphthalene and nonyl alcohols or a mixture of trimethylbenzenes and alky cyclohexanol esters.

According to the present invention, it is preferred that the hydrogenation reaction according to (ii) is carried out in the presence of a hydrogenation catalyst. In general, there are no specific restrictions concerning the nature of the hydrogenation catalyst provided the catalyst is able to catalyze the hydrogenation reaction according to (ii). Preferably, the hydrogenation catalyst comprises one or more metals active in hydrogenation, wherein more preferably, the one or more metals are selected from the group consisting of the transition metals and a combination of two or more thereof, wherein the hydrogenation catalyst more preferably comprises Pd, Rh, Ru, Ni, Re, Os, Ir, Pt, Au, Ag, and a combination of two or more thereof, more preferably Pd, Rh, Ru, Ni, and a combination of two or more thereof, wherein more preferably, the one or more metals comprise Pd, even more preferably consists of Pd.

Further, it is preferred that the one or more metals comprised in the hydrogenation catalyst is supported on a support preferably comprising Al, Si, C, O, Zr, Ca, Ti and a combination of two or more thereof, more preferably Al, Si, O, C and a combination of two or more thereof, wherein more preferably, the support comprises Al, Si, O and a combination thereof.

Further, it is preferred that the hydrogenation catalyst use in (ii) comprises a ligand. Generally, there are no specific restrictions regarding the nature of the ligand, provided that the hydrogenation catalyst comprising the ligand is able to catalyze the hydrogenation reaction according to (ii). Thus, the ligand may be charged or uncharged. Preferably, the ligand is selected from the group consisting of 1,5-cyclooctadiene (COD), tricyclohexylphosphin (PCy$_3$), 1,2-bis(di-tert-butyl-phosphinomethyl)benzene (DTBPP), tetrafluoroborate, chloride, n-tributylphosphine, triethylphosphine, methallyl, triphos, and a combination of two or more thereof, more preferably, the ligand is selected from the group consisting of 1,5-cyclooctadiene (COD), tricyclohexylphosphin PCy$_3$), 1,2-Bis(di-tert-butyl-phosphinomethyl)-benzene (DTBPP), tetrafluoroborate, chloride, and a combination of two or more thereof. Preferably, the hydrogenation reaction according to (ii) is carried out in the presence of a hydrogenation catalyst and in the presence of an additive, wherein the additive is preferably 1-butyl-3-methylimidazolium chloride (BMIMCl). In case the hydrogenation catalyst comprises Rh, 1,5-cyclooctadiene and tetrafluoroborate, it is particularly preferred to carry out the hydrogenation catalyst in the presence of 1-butyl-3-methylimidazolium chloride (BMIMCl).

As far as the temperature, at which the hydrogenation reaction according to (ii) is carried out is concerned, no specific restrictions exist provided that hydrogenation of the mixture provided in (i) takes place. Preferably, the hydrogenation reaction according to (ii) is carried out at a temperature in the range of from 20 to 200° C., preferably from 25 to 150° C., more preferably from 30 to 100° C., such as from 30 to 70° C. or from 40 to 80° C. or from 50 to 90° C. or from 60 to 100° C.

Also, as far as the pressure, at which the hydrogenation reaction according to (ii) is carried out is concerned, no specific restrictions exist provided that hydrogenation of the mixture provided in (i) takes place. Preferably, the hydrogenation reaction according to (ii) is carried out at a hydrogen pressure in the range of from 1 to 50 bar, preferably from 1 to 30 bar, more preferably from 1 to 20 bar, more preferably from 1 to 10 bar, such as from 1 to 3 bar or from 2 to 7 bar or from 3 to 10 bar.

As intermediates during the hydrogenation reaction according to (ii), the following intermediates according to formula (IIa-i) and/or (IIb-i) can be obtained:

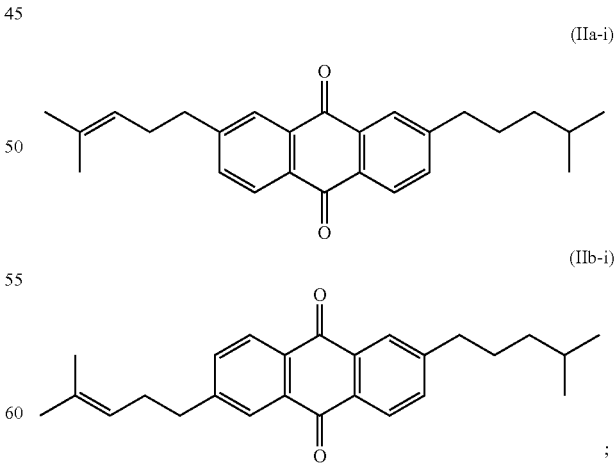

It is conceivable that these intermediates can be suitable isolated. Therefore, during the hydrogenation reaction according to (ii), a reaction mixture can be obtained which comprises the compounds of formula (IIa) and/or, preferably and, of formula (IIb), and the compounds of formula (IIa-i) and/or, preferably and, of formula (IIb-i);

the compounds of formula (IIa-i) and/or, preferably and, of formula (IIb-i), and the compounds of formula (Ia) and/or, preferably and, of formula (Ib)

the compounds of formula (IIa) and/or, preferably and, of formula (IIb), and the compounds of formula (Ia) and/or, preferably and, of formula (Ib).

Step (iii)

Preferably, the mixture obtained in (ii) is subjected to a treating with an inorganic base according to (iii), wherein a mixture comprising the compounds of formula (Ia) and/or, preferably and, formula (Ib) is obtained. Preferred inorganic bases include, but are not restricted to, alkali metal bases and alkaline earth metal bases, preferably hydroxides, more preferably alkali metal bases, more preferably alkali metal hydroxides, more preferably potassium and/or sodium hydroxides. The inorganic base used in (iii) is preferably selected from the group consisting of potassium hydroxide, sodium hydroxide, and a combination thereof, wherein the inorganic base more preferably comprises, more preferably consists of, potassium hydroxide.

Thus, it is particularly preferred that process for the preparation of a composition comprising a compound of formula (Ia) and/or, preferably and, a compound of formula (Ib) further comprising (iii) treating the mixture obtained in (ii) with an inorganic base, preferably selected from the group consisting of potassium hydroxide, sodium hydroxide, and a combination thereof, wherein the inorganic base more preferably comprises, more preferably consists of, potassium hydroxide, obtaining a mixture comprising the compounds of formula (Ia) and/or, preferably and, formula (Ib).

As far as the temperature, at which the treating according to (iii) is carried out is concerned, no specific restrictions exist provided that a mixture comprising the compounds of formula (Ia) and/or, preferably and, formula (Ib). Preferably, the treating according to (iii) is carried out at a temperature in the range of from 30 to 150° C., preferably from 40 to 100° C., more preferably from 45 to 70° C.

Further, it is preferred to crystallize the compound of formula (Ia) and/or, preferably and, a compound of formula (Ib) from the mixture obtained in (ii). It is also preferred to crystallize the compound of formula (Ia) and/or, preferably and, a compound of formula (Ib) from the mixture obtained in (iii). According to the present invention, it is particularly preferred that the process for the preparation of a composition comprising a compound of formula (Ia) and/or, preferably and, a compound of formula (Ib) further comprises crystallizing the compounds of formula (Ia) and/or, preferably and, formula (Ib) from the mixture obtained in (ii), or from the mixture obtained in (iii).

Also, the present invention relates to a mixture or a composition, comprising the compounds of formula (Ia) and/or, preferably and, formula (Ib), obtainable or obtained by the process as described above.

Preferred Uses

The compounds according to the present invention, preferably the compound of formula (Ia)

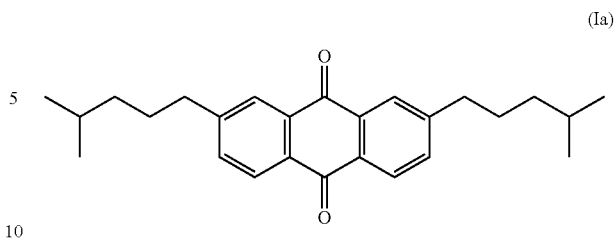

and/or, preferably and, the compound of formula (Ib)

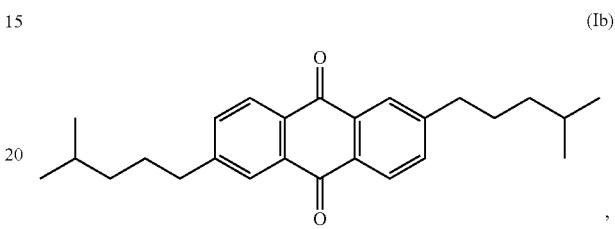

more preferably a composition comprising a compound of formula (Ia) and a compound of formula (Ib) as well as a compound of formula (IIa)

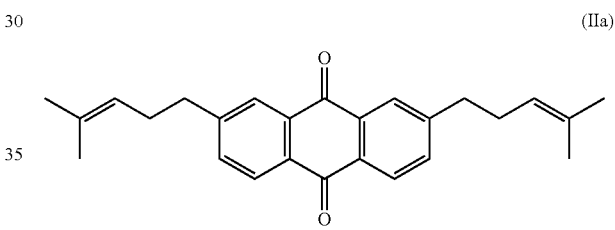

and/or, preferably and, a compound of formula (IIb)

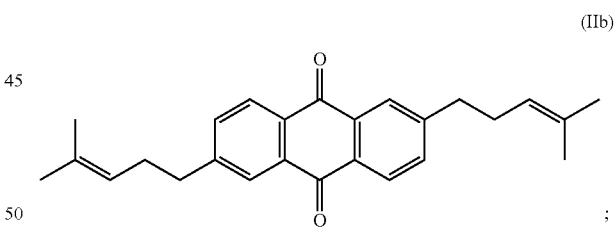

more preferably a mixture comprising a compound of formula (IIa) and a compound of formula (IIb) as described above, can be used for every conceivable purpose.

The present invention preferably relates to the use of a compound selected from the group consisting of the compound of formula (Ia), the compound of formula (Ib), and a combination thereof, preferably to the use of a composition comprising a compound of formula (Ia) and a compound of formula (Ib), for the preparation of hydrogen peroxide, preferably as anthraquinone compound in an anthraquinone process for the preparation hydrogen peroxide.

Further, it is conceivable to use a mixture comprising a compound of formula (IIa) and/or, preferably and, a compound of formula (IIb), wherein this mixture is preferably obtained from the oxidation reaction according to (c), more preferably from the separation according to (c"), for the preparation hydrogen peroxide, preferably as anthraquinone compound in an anthraquinone process for the preparation hydrogen peroxide.

Furthermore, is it conceivable to separate the compound of formula (IIa) and/or, preferably and, a compound of formula (IIb), from the mixture obtained from the oxidation reaction according to (c), more preferably from the separation according to (c"), and to use the separated compound of formula (IIa) and/or, preferably and, a compound of formula (IIb), for the preparation hydrogen peroxide, preferably as anthraquinone compound in an anthraquinone process for the preparation hydrogen peroxide.

Process for the Preparation of Hydrogen Peroxide

Without wanting to be bound by any theory, it is believed that the compounds according to the present invention, in particular the compositions of formula (Ia) and (Ib), are especially stable against ring-hydrogenation if used as anthraquinone starting materials in a process for the preparation of hydrogen peroxide; thus, these compounds are especially suitable in a process for the preparation of hydrogen peroxide.

Thus, the present invention relates to a process for the preparation of hydrogen peroxide, comprising
(I) providing a compound of formula (Ia)

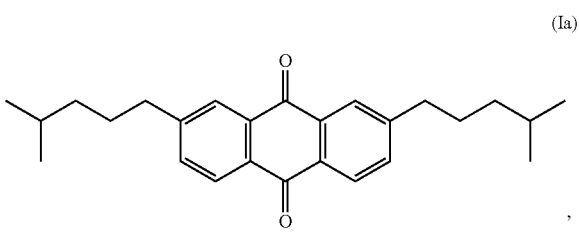 [SMILES: CC(C)CCCc1ccc2c(c1)C(=O)c1cc(CCCC(C)C)ccc1C2=O]

(Ia)

or a compound of formula (Ib)

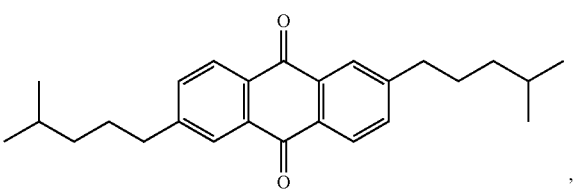

(Ib)

or a composition comprising a compound of formula (Ia) and a compound of formula (Ib), preferably a composition comprising a compound of formula (Ia) and a compound of formula (Ib), more preferably a composition as described above;
(II) preparing a mixture comprising the compound or the composition, preferably the composition, provided in (I) dissolved in an organic solvent, wherein the solvent is preferably selected from the group consisting of benzene, monoalkylated benzene, for example toluene or tert-butylbenzene, polyalkylated benzene, for example xylene, methylnaphthalene, alkyl phosphates, alkylcyclohexanol esters, N,N-dialkyl carbonamides, N-alkyl carbonamides, N-aryl carbonamides, N,N-dialkyl carbamates, tetraalkyl ureas, cycloalkyl ureas, phenylalkyl ureas, N-alkyl-2-pyrrolidones, N-alkyl caprolactams, alcohols having from 1 to 12 carbon atoms and a mixture of two or more thereof, more preferably selected from the group consisting of trimethylbenzene, tetramethylbenzene, alkyl phosphates, nonyl alcohols, N,N-dialkyl carbonamides, N,N-dialkyl carbamates, N-alkyl carbonamides, tetraalkyl ureas, cycloalkyl ureas, and a mixture of two or more thereof, and further comprising a hydrogenation catalyst;
(III) subjecting the mixture prepared in (II) to a hydrogenation reaction, obtaining a mixture comprising a compound of formula (VIIa)

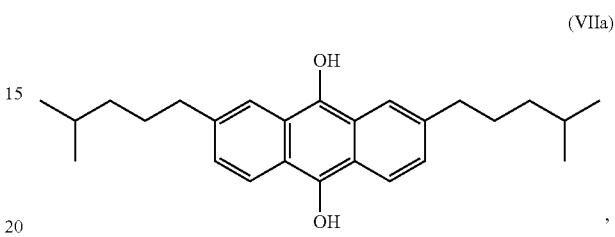

(VIIa)

or comprising a compound of formula (VIIb)

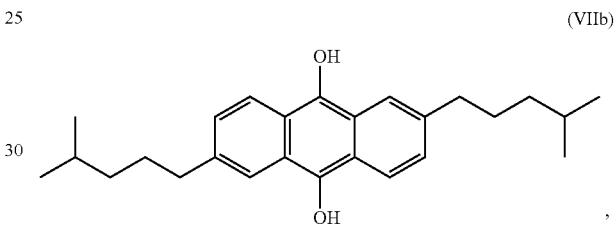

(VIIb)

or comprising a compound of formula (VIIa) and a compound formula (VIIb), preferably comprising a compound of formula (VIIa) and a compound of formula (VIIb);
(IV) subjecting the mixture obtained in (III) to an oxidation reaction in the presence of an oxygen containing gas, obtaining a mixture comprising the compound of formula (Ia), or the compound of formula (Ib), or the compound of formula (Ia) and the compound of formula (Ib), preferably comprising the compound of formula (Ia) and the compound of formula (Ib), and further comprising hydrogen peroxide;
(V) separating the hydrogen peroxide from the mixture obtained in (IV), obtaining a mixture comprising hydrogen peroxide and a mixture comprising the compound of formula (Ia), or the compound of formula (Ib), or the compound of formula (Ia) and the compound of formula (Ib), preferably comprising the compound of formula (Ia) and the compound of formula (Ib);
(VI) preferably subjecting the mixture obtained in (V), comprising the compound of formula (Ia), or the compound of formula (Ib), or the compound of formula (Ia) and the compound of formula (Ib), preferably comprising the compound of formula (Ia) and the compound of formula (Ib), to at least one repetition of the sequence of steps (III) to (V).

Generally, there are no specific restrictions how the compound of formula (Ia), or the compound of formula (Ib), or a composition comprising a compound of formula (Ia) and a compound of formula (Ib), preferably a composition comprising a compound of formula (Ia) and a compound of formula (Ib), more preferably a composition as described above, is provided in (I). For example, any conceivable process for synthesizing such a compound can be employed for providing the compound of formula (Ia), or of formula (Ib), or a composition comprising a compound of formula (Ia) and a compound of formula (Ib), or a composition as described above. Preferably, the composition comprising the compound of formula (Ia) and the compound of formula (Ib), preferably the composition as described above, is provided in (I) by a process a process for the preparation of a composition comprising a compound of formula (Ia) and a compound of formula (Ib) as described above.

According to the present invention, in (I), it is particularly preferred to provide a composition comprising the compound of formula (Ia) and the compound of formula (Ib), wherein at least 90 weight-%, preferably at least 92 weight-%, more preferably at least 94 weight-%, more preferably at least 96 weight-%, such as at least 99 weight-%, of the composition consists of the compounds of formula (Ia) and (Ib), and wherein the molar ratio of the compound of formula (Ia) relative to the compound of formula (Ib) is in the range of from 0.2:1 to 5:1, preferably from 0.3:1 to 3:1, more preferably from 0.5:1 to 2:1, more preferably from 0.8:1 to 1.2:1. Preferred ranges are, for example, from 0.8:1 to 1.0:1 or from 0.9:1 to 1.1:1 or from 1.0:1 to 1.2:1.

Thereafter, according to (II), a mixture is prepared, comprising the compound of formula (Ia), or the compound of formula (Ib), or a composition comprising the compound of formula (Ia) and the compound of formula (Ib), provided in (I) dissolved in an organic solvent, wherein the mixture further comprises a hydrogenation catalyst.

In (II), it is particularly preferred to prepare a mixture comprising a composition comprising the compound of formula (Ia) and the compound of formula (Ib) provided in (I), wherein at least 90 weight-%, preferably at least 92 weight-%, more preferably at least 94 weight-%, more preferably at least 96 weight-%, such as at least 99 weight-%, of the composition consists of the compounds of formula (Ia) and (Ib), and wherein the molar ratio of the compound of formula (Ia) relative to the compound of formula (Ib) is in the range of from 0.2:1 to 5:1, preferably from 0.3:1 to 3:1, more preferably from 0.5:1 to 2:1, more preferably from 0.8:1 to 1.2:1. Preferred ranges are, for example, from 0.8:1 to 1.0:1 or from 0.9:1 to 1.1:1 or from 1.0:1 to 1.2:1.

In general, there are no specific restrictions concerning the nature of the hydrogenation catalyst according to (II) provided the hydrogenation catalyst is able to catalyze the hydrogenation reaction according to (III). Preferably, the hydrogenation catalyst comprises one or more metals active in hydrogenation, wherein more preferably, the one or more metals are selected from the group consisting of the transition metals and a combination of two or more thereof, wherein the hydrogenation catalyst more preferably comprises Pd, Rh, Ru, Ni, Re, Os, Ir, Pt, Au, Ag, and a combination of two or more thereof, more preferably Pd, Rh, Ru, Ni, and a combination of two or more thereof, wherein more preferably, the one or more metals comprise Pd, even more preferably consist of Pd.

Further, it is preferred that one or more metals comprised in the hydrogenation catalyst according to (II) is supported on a support. As regards this support, no specific restrictions exist concerning the nature of the support provided that the hydrogenation catalyst is able to catalyze the hydrogenation reaction according to (III). Preferably, the support comprises at least on element selected from the group consisting of aluminum, barium, calcium, cerium, zirconium, titanium and silicon. More preferably the support comprises at least one compound selected from the group consisting of aluminum oxide, barium sulfate, calcium carbonate, cerium (IV) oxide, silicon oxide and zirconium(IV) oxide.

According to the present invention it is particularly preferred that the hydrogenation catalyst according to (II) comprises palladium preferably supported on a support preferably comprising at least on element selected from the group consisting of aluminum, barium, calcium, cerium, zirconium, titanium and silicon, more preferably comprising at least one compound selected from the group consisting of aluminum oxide, barium sulfate, calcium carbonate, cerium (IV) oxide, silicon oxide and zirconium(IV) oxide.

The mixture obtained in (II) is then subjected to a hydrogenation process. Concerning the temperature at which the hydrogenation reaction according to (III) is carried out, no specific restrictions exist provided that the hydrogenation reaction takes place. According to the present invention, it is preferred that the hydrogenation reaction according to (III) is carried out at a temperature in the range of from 20 to 200° C., preferably from 25 to 150° C., more preferably from 30 to 100° C.

According to the present invention, it is particularly preferred to subject a composition comprising the compound of formula (Ia) and the compound of formula (Ib), wherein at least 90 weight-%, preferably at least 92 weight-%, more preferably at least 94 weight-%, more preferably at least 96 weight-%, such as at least 99 weight-%, of the composition consists of the compounds of formula (Ia) and (Ib), and wherein the molar ratio of the compound of formula (Ia) relative to the compound of formula (Ib) is in the range of from 0.2:1 to 5:1, preferably from 0.3:1 to 3:1, more preferably from 0.5:1 to 2:1, more preferably from 0.8:1 to 1.2:1, to a hydrogenation reaction according to (III), wherein a mixture comprising the compound of formula (VIIa) and the compound of formula (VIIb) is obtained, wherein the molar ratio of the compound of formula (VIIa) relative to the compound of formula (VIIb) is in the range of from 0.2:1 to 5:1, preferably from 0.3:1 to 3:1, more preferably from 0.5:1 to 2:1, more preferably from 0.8:1 to 1.2:1.

Optionally, (III) further comprises separating the hydrogenation catalyst from the mixture comprising a compound of formula (VIIa)

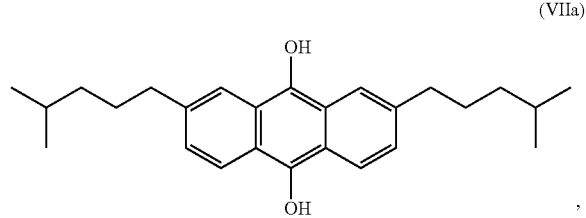 [SMILES: CC(C)CCCc1ccc2c(O)c3ccc(CCCC(C)C)cc3c(O)c2c1]

(VIIa)

or comprising a compound of formula (VIIb)

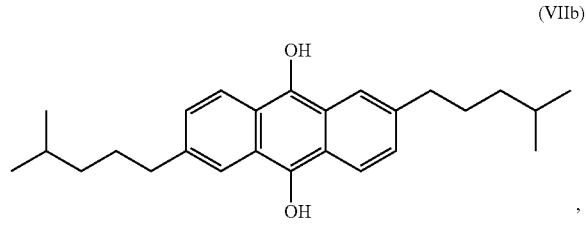 [SMILES: CC(C)CCCc1ccc2c(O)c3cc(CCCC(C)C)ccc3c(O)c2c1]

(VIIb)

or comprising a compound of formula (VIIa) and a compound formula (VIIb), preferably comprising a compound of formula (VIIa) and a compound of formula (VIIb).

The mixture obtained in (III), preferably after separation of the hydrogenation catalyst is subjected to an oxidation reaction according to (IV). It is particularly preferred that the mixture comprises the compound of formula (VIIa) and the compound of formula (VIIb) obtained in (III), wherein the molar ratio of the compound of formula (VIIa) relative to the compound of formula (VIIb) is in the range of 0.1.1 to 5:1, preferably from 0.3:1 to 3:1, more preferably from 0.5:1 to 2:1, even more preferably from 0.8:1 to 1.2:1, is subjected to an oxidation reaction according to (IV), wherein a mixture comprising the compound of formula (Ia) and the compound of formula (Ib), wherein the molar ratio of the compound of formula (Ia) relative to the compound of formula (Ib) is in the range of from 0.2:1 to 5:1, preferably from 0.3:1 to 3:1, more preferably from 0.5:1 to 2:1, more preferably from 0.8:1 to 1.2:1 is obtained, and wherein the mixture further comprises hydrogen peroxide.

Further, the mixture obtained in the oxidation reaction according to (IV) is subjected to a separation step, wherein a mixture comprising hydrogen peroxide and a mixture comprising the compound of formula (Ia), or the compound of formula (Ib), or the compound of formula (Ia) and the compound of formula (Ib), preferably comprising the compound of formula (Ia) and the compound of formula (Ib) are obtained.

As regards the separation according to (V), all methods of separating the hydrogen peroxide from the mixture obtained in (V) are conceivable. Preferably, the hydrogen peroxide is separated from the mixture obtained in (IV) by extraction, more preferably by extraction with an aqueous solution, more preferably by extraction with water, wherein a mixture comprising hydrogen peroxide obtained is obtained.

Preferably, at least 1 weight-%, more preferably at least 5 weight-%, more preferably at least 10 weight-%, more preferably at least 20 weight-%, more preferably at least 30 weight-% of the mixture comprising hydrogen peroxide obtained according to (V) consist of hydrogen peroxide.

After the separation according to (V), the mixture obtained in (V) comprising the compound of formula (Ia), or the compound of formula (Ib), or the compound of formula (Ia) and the compound of formula (Ib), preferably comprising the compound of formula (Ia) and the compound of formula (Ib), is subjected to at least one repetition of the sequence of steps (III) to (V).

It is particular preferred that the mixture obtained in (V) comprising the compound of formula (Ia) and the compound of formula (Ib), is subjected to a hydrogenation reaction according to (III), wherein mixture obtained in (III) is subjected to an oxidation reaction according to (IV), and wherein the mixture obtained in (IV) is subjected to a separation step according to (V), and wherein the resulting mixture obtained in (V) can be subjected to a further repetition of the sequence of steps (III) to (V).

The present invention also relates to a mixture comprising hydrogen peroxide, obtainable or obtained by a process for the preparation of hydrogen peroxide as described above, preferably obtainable or obtained in step (V) of a process for the preparation of hydrogen peroxide as described above.

Further, it may be conceivable to carry out a process for the preparation of hydrogen peroxide by use of a compound of formula (IIa) or a compound of formula (IIb) or a mixture comprising a compound of formula (IIa) or a compound of formula (IIb), preferably a composition comprising a compound of formula (IIa) or a compound of formula (IIb).

Thus, it may be conceivable to carry out a process for the preparation of hydrogen peroxide, comprising
(A) providing a compound of formula (IIa)

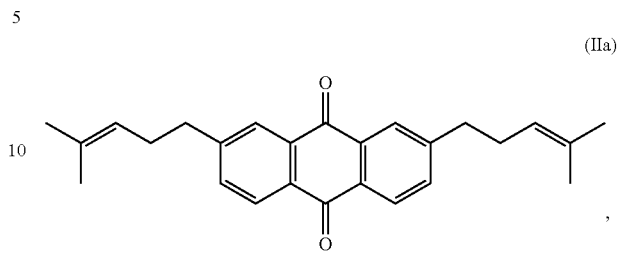

(IIa)

or a compound of formula (IIb)

(IIb)

or a mixture comprising a compound of formula (IIa) and a compound of formula (Ib), preferably a mixture comprising a compound of formula (IIa) and a compound of formula (IIb), more preferably a composition as described above;
(B) preparing a mixture comprising the compound or the composition, preferably the composition, provided in (A) dissolved in an organic solvent, wherein the solvent is preferably selected from the group consisting of benzene, monoalkylated benzene, preferably toluene or tert-butylbenzene, polyalkylated benzene, for example xylene, methylnaphthalene, alkyl phosphates, alkylcyclohexanol esters, N,N-dialkyl carbonamides, N-alkyl carbonamides, N-aryl carbonamides, N,N-dialkyl carbamates, tetraalkyl ureas, cycloalkyl ureas, phenylalkyl ureas, N-alkyl-2-pyrrolidones, N-alkyl caprolactams, alcohols having from 1 to 12 carbon atoms and a mixture of two or more thereof, more preferably selected from the group consisting of trimethylbenzene, tetramethylbenzene, alkyl phosphates, nonyl alcohols, N,N-dialkyl carbonamides, N,N-dialkyl carbamates, N-alkyl carbonamides, tetraalkyl ureas, cycloalkyl ureas, and a mixture of two or more thereof, and further comprising a hydrogenation catalyst;
(C) subjecting the mixture prepared in (B) to a hydrogenation reaction, obtaining a mixture comprising a compound of formula (VIIa)

(VIIa)

or comprising a compound of formula (VIIb)

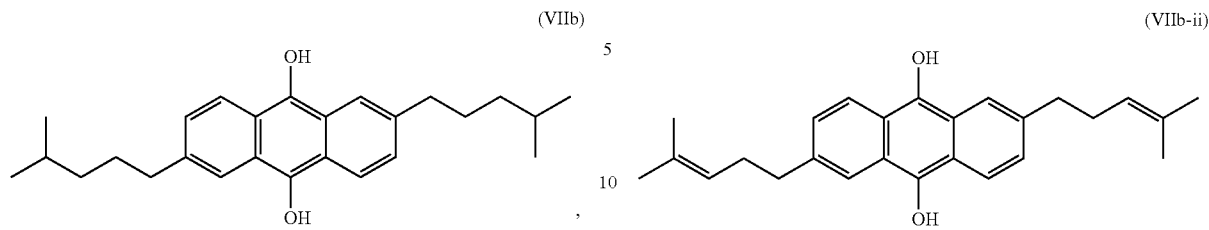
(VIIb)

or comprising a compound of formula (VIIa) and a compound formula (VIIb), preferably comprising a compound of formula (VIIa) and a compound of formula (VIIb);

(D) subjecting the mixture obtained in (C) to an oxidation reaction in the presence of an oxygen containing gas, obtaining a mixture comprising the compound of formula (Ia), or the compound of formula (Ib), or the compound of formula (Ia) and the compound of formula (Ib), preferably comprising the compound of formula (Ia) and the compound of formula (Ib), and further comprising hydrogen peroxide;

(E) separating the hydrogen peroxide from the mixture obtained in (D), obtaining a mixture comprising hydrogen peroxide and a mixture comprising the compound of formula (Ia), or the compound of formula (Ib), or the compound of formula (Ia) and the compound of formula (Ib), preferably comprising the compound of formula (Ia) and the compound of formula (Ib);

(F) preferably subjecting the mixture obtained in (E), comprising the compound of formula (Ia), or the compound of formula (Ib), or the compound of formula (Ia) and the compound of formula (Ib), preferably comprising the compound of formula (Ia) and the compound of formula (Ib), to at least one repetition of the sequence of steps (C) to (E).

In particular in case the process for the preparation of hydrogen peroxide is carried out by use of a compound of formula (IIa) or a compound of formula (IIb) or a mixture comprising a compound of formula (IIa) or a compound of formula (IIb), preferably a composition comprising a compound of formula (IIa) or a compound of formula (IIb), intermediate compounds of formula (VIIa-ii)

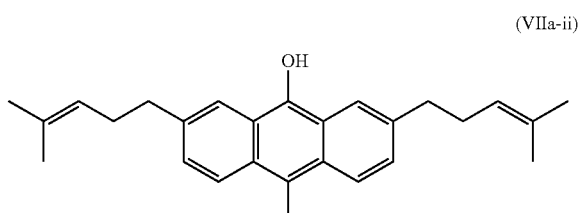
(VIIa-ii)

and/or, preferably and, of formula (VIIb-ii)

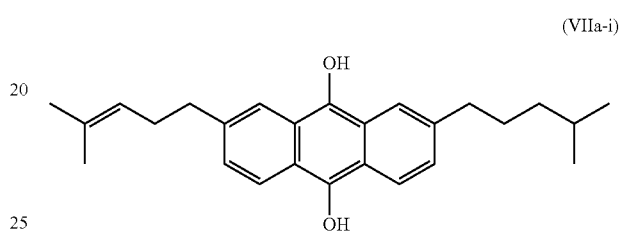
(VIIb-ii)

can be obtained, and further, intermediate compounds of formula (VIIa-i)

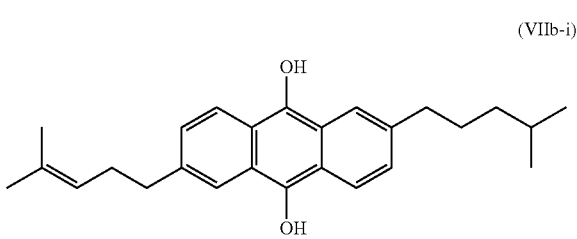 [SMILES: CC(C)=CCCc1ccc2c(O)c3cc(CCCC(C)C)ccc3c(O)c2c1]
(VIIa-i)

and/or, preferably and, of compound (VIIb-i)

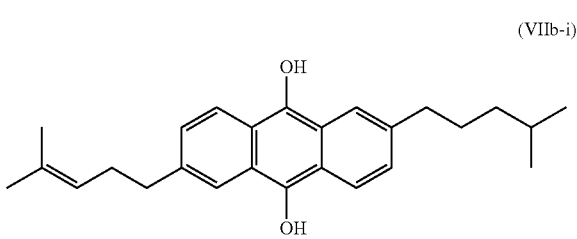 [SMILES: CC(C)=CCCc1ccc2c(O)c3cc(CCCC(C)C)ccc3c(O)c2c1]
(VIIb-i)

can be obtained. Therefore, during the hydrogenation reaction according to (C), a reaction mixture may be obtained which comprises
- the compounds of formula (IIa) and/or, preferably and, of formula (IIb), and the compounds of formula (VIIa-ii) and/or, preferably and, of formula (VIIb-ii);
- the compounds of formula (IIa) and/or, preferably and, of formula (IIb), and the compounds of formula (VIIa-ii) and/or, preferably and, of formula (VIIb-ii), and the compounds of formula (VIIa-i) and/or, preferably and, of formula (VIIb-i);
- the compounds of formula (IIa) and/or, preferably and, of formula (IIb), and the compounds of formula (VIIa-ii) and/or, preferably and, of formula (VIIb-ii), and the compounds of formula (VIIa-i) and/or, preferably and, of formula (VIIb-i), and the compounds of formula (VIIa) and/or, preferably and, of formula (VIIb);
- the compounds of formula (VIIa-ii) and/or, preferably and, of formula (VIIb-ii), and the compounds of formula (VIIa-i) and/or, preferably and, of formula (VIIb-i);
- the compounds of formula (VIIa-ii) and/or, preferably and, of formula (VIIb-ii), and the compounds of formula (VIIa-i) and/or, preferably and, of formula (VIIb-i), and the compounds of formula (VIIa) and/or, preferably and, of formula (VIIb);
- the compounds of formula (VIIa-i) and/or, preferably and, of formula (VIIb-i), and the compounds of formula (VIIa) and/or, preferably and, of formula (VIIb).

The mixture comprising hydrogen peroxide according to the present invention can be used for every conceivable purpose. Preferably, the mixture comprising hydrogen peroxide according to the present invention is used for the preparation of propylene oxide, a propylene glycol, a polyol and/or a polyurethane. Thus, the present invention relates to the use of a mixture comprising hydrogen peroxide as described above for the preparation of propylene oxide, a propylene glycol, a polyol and/or a polyurethane.

The present invention is further illustrated by the following embodiments and combination of embodiments as indicated by all respective dependencies and references:

1. A compound of formula (Ia)

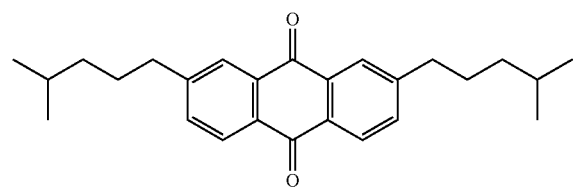

(Ia)

2. A compound of formula (Ib)

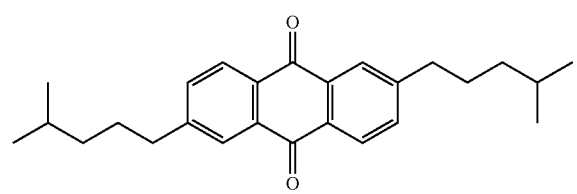

(Ib)

3. A composition comprising a compound of formula (Ia)

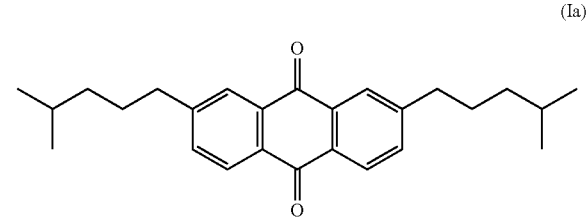

(Ia)

and a compound of formula (Ib)

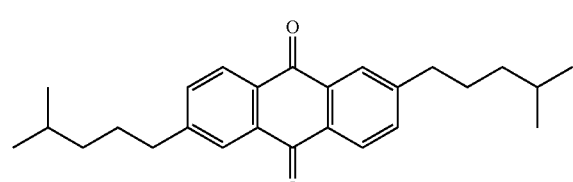

(Ib)

4. The composition of embodiment 3, wherein at least 90 weight-%, preferably at least 92 weight-%, more preferably at least 94 weight-%, more preferably at least 96 weight-% of the composition consist of the compounds of formula (Ia) and formula (Ib).

5. The composition of embodiment 3 or 4, wherein the molar ratio of the compound of formula (Ia) relative to the compound of formula (Ib) is in the range of from 0.2:1 to 5:1, preferably from 0.3:1 to 3:1, more preferably from 0.5:1 to 2:1, more preferably from 0.8:1 to 1.2:1.

6. The composition of any of embodiments 3 to 5, having a solubility of at least 1.0 mol/l, preferably of at least 1.4 mol/l, more preferably in the range of from 1.4 to 1.8 mol/l, in a solvent mixture of which at least 99.9 weight-% consist of ortho-xylene and diisobutyl carbinol with a molar ratio of the ortho-xylene relative to the diisobutyl carbinol in the range of from 0.99:1 to 1.01:1, wherein said solubility refers to the molar amount of the compound of formula (Ia) plus the molar amount of the compound of formula (Ib) dissolved in 1 l of the solvent mixture at a temperature in the range of from 20 to 23° C. and at a pressure in the range of from 0.9 to 1.1 bar.

7. The composition of any of embodiments 3 to 6, wherein at least 90 weight-%, preferably at least 92 weight-%, more preferably at least 99 weight-% of the compound of formula (Ia) and at least 94 weight-%, preferably at least 96 weight-%, more preferably at least 99 weight-% of the compound of formula (Ib) are present in solid form, preferably in solid crystalline form.

8. The composition of any of embodiments 3 to 7, being at least partially, preferably completely, dissolved in a solvent, wherein the solvent is preferably selected from the group consisting of benzene, monoalkylated benzene, preferably toluene or tert-butylbenzene, polyalkylated benzene, preferably xylene, methylnaphthalene, alkyl phosphates, alkylcyclohexanol esters, N,N-dialkyl carbonamides, N-alkyl carbonamides, N-aryl carbonamides, N,N-dialkyl carbamates, tetraalkyl ureas, cycloalkyl ureas, phenylalkyl ureas, N-alkyl-2-pyrrolidones, N-alkyl caprolactams, alcohols having from 1 to 12 carbon atoms and a mixture of two or more thereof, more preferably selected from the group consisting of trimethylbenzene, tetramethylbenzene, alkyl phosphates, nonyl alcohols, N,N-dialkyl carbonamides, N,N-dialkyl carbamates, N-alkyl carbonamides, tetraalkyl ureas, cycloalkyl ureas, and a mixture of two or more thereof.

9. A solution comprising a compound of formula (Ia)

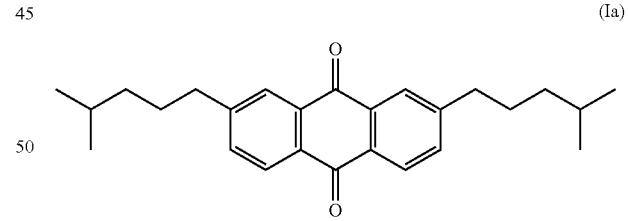

(Ia)

and/or, preferably and, a compound of formula (Ib)

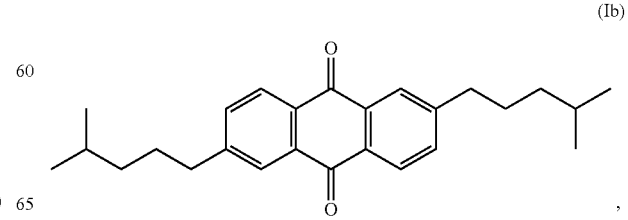

(Ib)

and further comprising a solvent, wherein the molar ratio of the compound of formula (Ia) relative to the compound of formula (Ib) is preferably in the range of from 0.2:1 to 5:1, preferably from 0.3:1 to 3:1, more preferably from 0.5:1 to 2:1, more preferably from 0.8:1 to 1.2:1, wherein the solvent is preferably selected from the group consisting of benzene, monoalkylated benzene, preferably toluene or tert-butylbenzene, polyalkylated benzene, preferably xylene, methylnaphthalene, alkyl phosphates, alkylcyclohexanol esters, N,N-dialkyl carbonamides, N-alkyl carbonamides, N-aryl carbonamides, N,N-dialkyl carbamates, tetraalkyl ureas, cycloalkyl ureas, phenylalkyl ureas, N-alkyl-2-pyrrolidones, N-alkyl caprolactams, alcohols having from 1 to 12 carbon atoms and a mixture of two or more thereof, more preferably selected from the group consisting of trimethylbenzene, tetramethylbenzene, alkyl phosphates, nonyl alcohols, N,N-dialkyl carbonamides, N,N-dialkyl carbamates, N-alkyl carbonamides, tetraalkyl ureas, cycloalkyl ureas, and a mixture of two or more thereof, and wherein the concentration of the sum of the compounds of formula (Ia) and formula (Ib) is preferably in the range of from 0.6 to 2.2 mol/l, more preferably in the range of from 0.8 to 2.0 mol/l, more preferably in the range of from 1.0 to 1.8 mol/l.

10. A process for the preparation of a composition comprising a compound of formula (Ia)

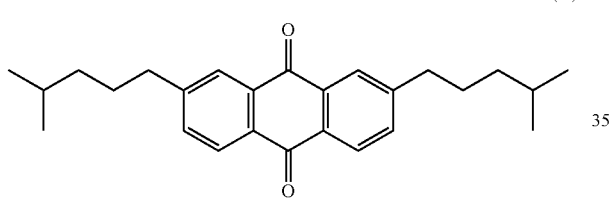
(Ia)

and/or, preferably and, a compound of formula (Ib)

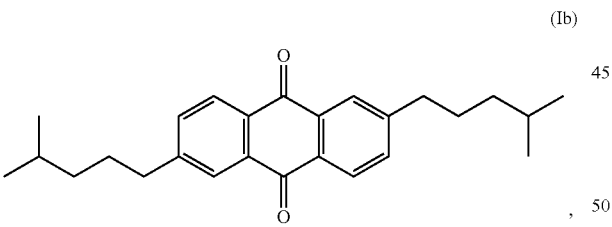
(Ib)

said process comprising
(i) providing a mixture comprising a compound of formula (IIa)

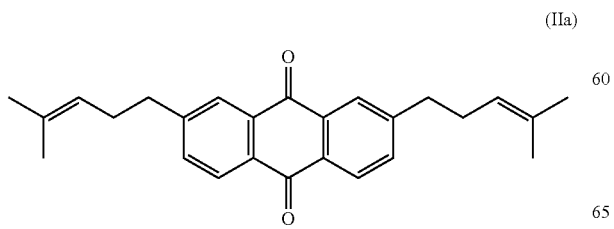
(IIa)

and/or, preferably and, a compound of formula (IIb)

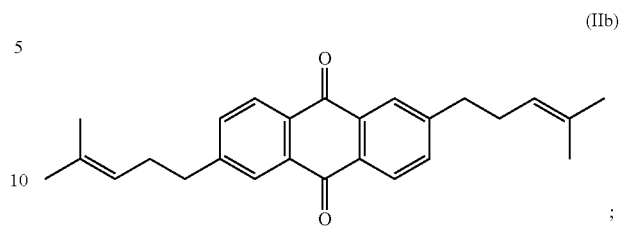
(IIb)

(ii) subjecting the mixture provided in (i) to a hydrogenation reaction, preferably in the presence of a hydrogenation catalyst.

11. The process of embodiment 10, wherein (i) comprises
(a) providing a compound of formula (III)

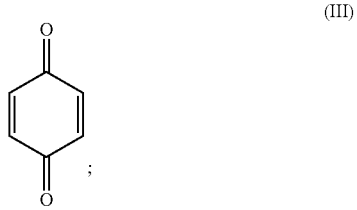
(III)

(b) reacting, preferably in a solvent, the compound of formula (III) provided in (a) with a compound of formula (IV)

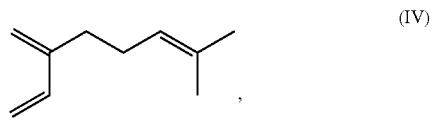
(IV)

obtaining a mixture comprising a compound of formula (Va)

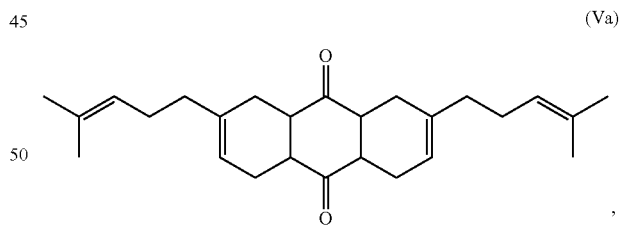
(Va)

and/or, preferably and, a compound of formula (Vb)

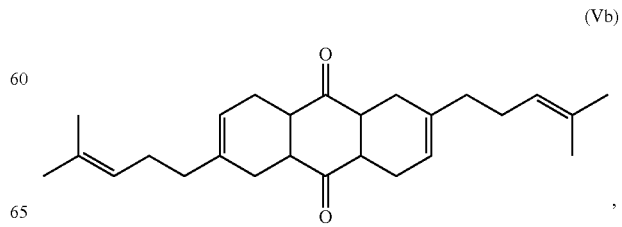
(Vb)

(c) subjecting the mixture obtained in (b) to an oxidation reaction, preferably in the presence of an oxygen containing gas, preferably selected from the consisting of oxygen, air, and lean air, and preferably in the presence of an inorganic base, preferably selected from the group consisting of potassium hydroxide, sodium hydroxide, and a combination thereof, obtaining a mixture comprising the compound of formula (IIa) and/or, preferably and, the compound of formula (IIb).

12. The process of embodiment 11, wherein in (a), the compound of formula (III) is provided by a method comprising
(a.1) providing a compound of formula (VI)

(a.2) subjecting the compound of formula (VI) provided in (a.1), preferably in an organic solvent, to a dehydrogenation reaction, preferably in the presence of a dehydrogenation catalyst.

13. The process of embodiment 12, wherein the dehydrogenation reaction according to (a.2) is carried out in the presence of a dehydrogenation catalyst, wherein the dehydrogenation catalyst comprises one or more elements selected from the group of the transition metals and a combination of two or more thereof, wherein the dehydrogenation catalyst more preferably comprises copper and at least one additional element selected from the group consisting of lithium, zinc, zirconium, aluminum, and a combination of two or more thereof, wherein the dehydrogenation catalyst preferably comprises a combination of copper, and lithium or a combination of copper, zinc, zirconium and aluminum.

14. The process of embodiment 12 or 13, wherein the organic solvent according to (a.2) is selected from the group consisting of benzene, monoalkylated benzene, preferably toluene or tert-butylbenzene, polyalkylated benzene, preferably xylene, methylnaphthalene, alkyl phosphates, alkylcyclohexanol esters, N,N-dialkyl carbonamides, N-alkyl carbonamides, N-aryl carbonamides, N,N-dialkyl carbamates, tetraalkyl ureas, cycloalkyl ureas, phenylalkyl ureas, N-alkyl-2-pyrrolidones, N-alkyl caprolactams, alcohols having from 1 to 12 carbon atoms, and a mixture of two or more thereof, preferably selected from the group consisting of, trimethylbenzene, tetramethylbenzene, alkyl phosphates, nonyl alcohols, N,N-dialkyl carbonamides, N,N-dialkyl carbamates, N-alkyl carbonamides, tetraalkyl ureas, cycloalkyl ureas, and a mixture of two or more thereof.

15. The process of any of embodiments 12 to 14, wherein the temperature at the beginning of the hydrogenation reaction according to (a.2) is in the range of from 10 to 120° C., preferably from 20 to 90° C., more preferably from 30 to 70° C.

16. The process of any of embodiments 11 to 15, wherein the reaction according to (b) is carried out in a solvent, preferably in an organic solvent, more preferably selected from the group consisting of benzene, monoalkylated benzene, preferably toluene or tert-butylbenzene, polyalkylated benzene, preferably xylene, methylnaphthalene, alkyl phosphates, alkylcyclohexanol esters, N,N-dialkyl carbonamides, N-alkyl carbonamides, N-aryl carbonamides, N,N-dialkyl carbamates, tetraalkyl ureas, cycloalkyl ureas, phenylalkyl ureas, N-alkyl-2-pyrrolidones, N-alkyl caprolactams, alcohols having from 1 to 12 carbon atoms, and a mixture of two or more thereof, more preferably selected from the group consisting of trimethylbenzene, tetramethylbenzene, alkyl phosphates, nonyl alcohols, N,N-dialkyl carbonamides, N,N-dialkyl carbamates, N-alkyl carbonamides, tetraalkyl ureas, cycloalkyl ureas, and a mixture of two or more thereof.

17. The process of any of embodiments 11 to 16, wherein at the beginning of the reaction according to (b), the molar ratio of the compound of formula (IV) relative to the compound of formula (III) is in the range of from 1:1 to 10:1, preferably from 1:1 to 5:1, more preferably from 1:1 to 3:1, more preferably from 1:1 to 2:1.

18. The process of any of embodiments 11 to 17, wherein the reaction according to (b) is carried out at a temperature in the range of from 50 to 250° C., preferably from 60 to 200° C., more preferably from 70 to 150° C., more preferably from 75° C. to 100° C.

19. The process of any of embodiments 11 to 18, wherein the reaction according to (b) is carried out for a period of time in the range of from 12 to 480 h, preferably from 16 to 240 h, more preferably from 18 to 120 h, more preferably from 20 to 72 h 20. The process of any of embodiments 11 to 19, wherein after (b) and prior to (c), the process further comprises
(b') separating the compounds of formula (Va) and/or, preferably and, formula (Vb) from the mixture obtained in (b), obtaining a mixture comprising the compounds of formula (Va) and/or, preferably and, formula (Vb), wherein preferably at least 90 weight-%, more preferably at least 92 weight-%, more preferably at least 94 weight-%, more preferably at least 96 weight-% of the obtained mixture consist of the compounds of formula (Va) and (Vb).

21. The process of any of embodiments 11 to 19, wherein prior to (c), the compounds of formula (Va) and/or, preferably and, formula (Vb) are not separated from the mixture obtained in (b).

22. The process of any of embodiments 11 to 21, wherein the oxidation reaction according to (c) is carried out in a solvent, preferably an organic solvent, wherein the solvent is more preferably selected from the group consisting of benzene, monoalkylated benzene, preferably toluene or tert-butylbenzene, polyalkylated benzene, preferably xylene, methylnaphthalene, alkyl phosphates, alkylcyclohexanol esters, N,N-dialkyl carbonamides, N-alkyl carbonamides, N-aryl carbonamides, N,N-dialkyl carbamates, tetraalkyl ureas, cycloalkyl ureas, phenylalkyl ureas, N-alkyl-2-pyrrolidones, N-alkyl caprolactams, alcohols having from 1 to 12 carbon atoms, and a mixture of two or more thereof, more preferably selected from the group consisting of trimethylbenzene, tetramethylbenzene, alkyl phosphates, nonyl alcohols, N,N-dialkyl carbonamides, N,N-dialkyl carbamates, N-alkyl carbonamides, tetraalkyl ureas, cycloalkyl ureas, alcohols having from 1 to 12 carbon atoms, and a mixture of two or more thereof.

23. The process of any of embodiments 11 to 22, wherein the temperature at the beginning of the oxidation reaction according (c) is the range of from 30 to 150° C., preferably from 40 to 100° C., more preferably from 50 to 90° C., more preferably from 55 to 80° C.

24. The process of any of embodiments 11 to 23, wherein the oxidation reaction according to (c) is carried out for a period of time in the range of from 0.2 to 24 h, preferably from 0.5 to 12 h, more preferably from 1 to 8 h.

25. The process of any of embodiments 11 to 24, wherein after (c) and prior to (ii) the process further comprises
   (c') separating the compounds of formula (IIa) and/or, preferably and, formula (IIb) from the mixture obtained in (c), obtaining a mixture comprising the compounds of formula (IIa) and/or, preferably and, formula (IIb), wherein preferably at least 90 weight-%, more preferably at least 92 weight-%, more preferably at least 94 weight-%, more preferably at least 96 weight-% of the obtained mixture consist of the compounds of formula (IIa) and (IIb), wherein said separating preferably comprises crystallizing the compounds of formula (IIa) and/or, preferably and, formula (IIb).

26. The process of any of embodiments 11 to 24, wherein after (c) and prior to (ii), the compounds of formula (IIa) and/or, preferably and, formula (II) are not separated from the mixture obtained in (c), wherein, if the oxidation reaction according to (c) is carried out in the presence of an inorganic base, the process after (c) and prior to (ii) preferably further comprises
   (c") separating the inorganic base at least partially, preferably completely, from the mixture obtained in (c), obtaining a mixture being depleted in the inorganic base and comprising the compounds of formula (IIa) and/or, preferably and, formula (IIb), wherein said separating preferably comprises extracting the inorganic base, preferably with water.

27. The process of any of embodiments 10 to 26, wherein the hydrogenation reaction according to (ii) is carried out in a solvent, preferably an organic solvent, wherein the solvent is more preferably selected from the group consisting of benzene, monoalkylated benzene, preferably toluene or tert-butylbenzene, polyalkylated benzene, preferably xylene, methylnaphthalene, alkyl phosphates, alkylcyclohexanol esters, N,N-dialkyl carbonamides, N-alkyl carbonamides, N-aryl carbonamides, N,N-dialkyl carbamates, tetraalkyl ureas, cycloalkyl ureas, phenylalkyl ureas, N-alkyl-2-pyrrolidones, N-alkyl caprolactams, alcohols having from 1 to 12 carbon atoms, and a mixture of two or more thereof, more preferably selected from the group consisting of trimethylbenzene, tetramethylbenzene, alkyl phosphates, nonyl alcohols, N,N-dialkyl carbonamides, N,N-dialkyl carbamates, N-alkyl carbonamides, tetraalkyl ureas, cycloalkyl ureas, and a mixture of two or more thereof.

28. The process of any of embodiments 10 to 27, wherein the hydrogenation reaction according to (ii) is carried out in the presence of a hydrogenation catalyst and wherein the hydrogenation catalyst comprises one or more metals active in hydrogenation, preferably comprising one or more elements selected from the group consisting of the transition metals and a combination of two or more thereof, wherein the hydrogenation catalyst more preferably more preferably is selected from the croup consisting of Pd, Rh, Ru, Ni, Re, Os, Ir, Pt, Au, Ag, Zr, more preferably selected from the croup consisting of Pd, Rh, Ru, Ni and a combination of two or more thereof wherein the one or more metals more preferably comprise, more preferably consist of, Pd.

29. The process of any of embodiments 10 to 28, wherein the hydrogenation reaction according to (ii) is carried out at a temperature in the range of from 20 to 100° C., preferably from 25 to 80° C., more preferably from 30 to 70° C.

30. The process of any of embodiments 10 to 29, wherein the hydrogenation reaction according to (ii) is carried out at a hydrogen pressure in the range of from 1 to 50 bar, preferably from 1 to 30 bar, more preferably from 1 to 20 bar, more preferably from 1 to 10 bar.

31. The process of any of embodiments 10 to 30, further comprising
   (iii) treating the mixture obtained in (ii) with an inorganic base, preferably selected from the croup consisting of potassium hydroxide, sodium hydroxide, and a combination thereof, wherein the inorganic base more preferably comprises, more preferably consists of, potassium hydroxide, obtaining a mixture comprising the compounds of formula (Ia) and/or, preferably and, formula (Ib).

32. The process of embodiment 31, wherein the treating according to (iii) is carried out at a temperature in the range of from 30 to 150° C., preferably from 40 to 100° C., more preferably from 45 to 70° C.

33. The process of any of embodiments 10 to 30, further comprising crystallizing the compounds of formula (Ia) and/or, preferably and, formula (Ib) from the mixture obtained in (ii), or of claim 31 or 32, further comprising crystallizing the compounds of formula (Ia) and/or, preferably and, formula (Ib) from the mixture obtained in (iii).

34. A mixture or a composition, comprising the compounds of formula (Ia)

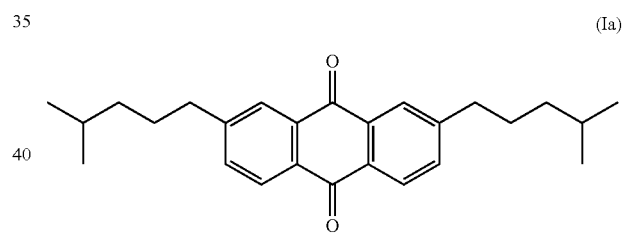

(Ia)

and/or, preferably and, a compound of formula (Ib)

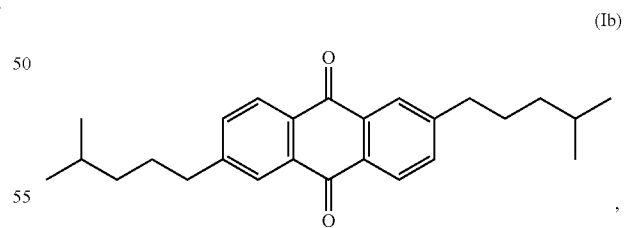

(Ib)

obtainable or obtained by a process according to any of embodiments 10 to 33.

35. Use of a compound selected from the group consisting of the compound according to embodiment 1, the compound of embodiment 2, and a combination thereof, preferably of a composition according to any of embodiments 3 to 8, for the preparation of hydrogen peroxide, preferably as anthraquinone compound in an anthraquinone process for the preparation hydrogen peroxide.

36. A process for the preparation of hydrogen peroxide, comprising
(I) providing a compound of formula (Ia)

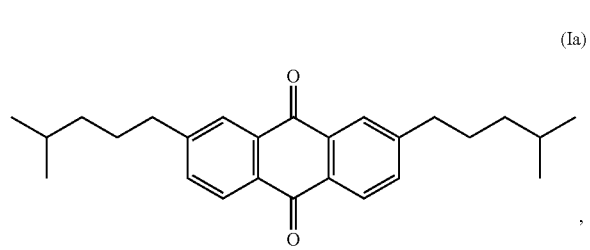 [SMILES: CC(C)CCCc1ccc2c(c1)C(=O)c1cc(CCCC(C)C)ccc1C2=O]

or a compound of formula (Ib)

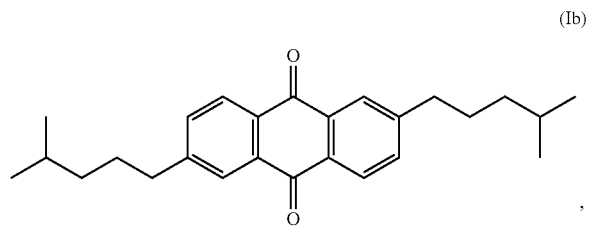 [SMILES: CC(C)CCCc1ccc2c(c1)C(=O)c1ccc(CCCC(C)C)cc1C2=O]

or a composition comprising a compound of formula (Ia) and a compound of formula (Ib), preferably a composition comprising a compound of formula (Ia) and a compound of formula (Ib), more preferably a composition according to any of embodiments 3 to 8;
(II) preparing a mixture comprising the compound or the composition, preferably the composition, provided in (I) dissolved in an organic solvent, wherein the solvent is preferably selected from the group consisting of benzene, monoalkylated benzene, preferably toluene or tert-butylbenzene, polyalkylated benzene, preferably xylene, methylnaphthalene, alkyl phosphates, alkylcyclohexanol esters, N,N-dialkyl carbonamides, N-alkyl carbonamides, N-aryl carbonamides, N,N-dialkyl carbamates, tetraalkyl ureas, cycloalkyl ureas, phenylalkyl ureas, N-alkyl-2-pyrrolidones, N-alkyl caprolactams, alcohols having from 1 to 12 carbon atoms and a mixture of two or more thereof, more preferably selected from the group consisting of trimethylbenzene, tetramethylbenzene, alkyl phosphates, nonyl alcohols, N,N-dialkyl carbonamides, N,N-dialkyl carbamates, N-alkyl carbonamides, tetraalkyl ureas, cycloalkyl ureas, and a mixture of two or more thereof, and further comprising a hydrogenation catalyst;
(III) subjecting the mixture prepared in (II) to a hydrogenation reaction, obtaining a mixture comprising a compound of formula (VIIa)

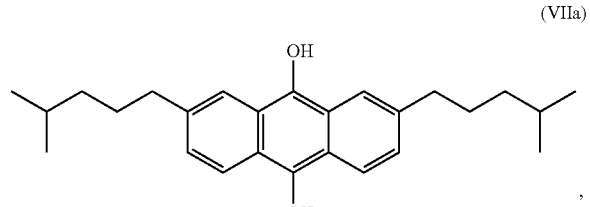

or comprising a compound of formula (VIIb)

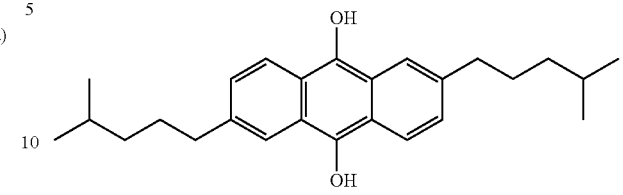

or comprising a compound of formula (VIIa) and a compound formula (VIIb), preferably comprising a compound of formula (VIIa) and a compound of formula (VIIb);
(IV) subjecting the mixture obtained in (III) to an oxidation reaction in the presence of an oxygen containing gas, obtaining a mixture comprising the compound of formula (Ia), or the compound of formula (Ib), or the compound of formula (Ia) and the compound of formula (Ib), preferably comprising the compound of formula (Ia) and the compound of formula (Ib), and further comprising hydrogen peroxide;
(V) separating the hydrogen peroxide from the mixture obtained in (IV), obtaining a mixture comprising hydrogen peroxide and a mixture comprising the compound of formula (Ia), or the compound of formula (Ib), or the compound of formula (Ia) and the compound of formula (Ib), preferably comprising the compound of formula (Ia) and the compound of formula (Ib);
(VI) preferably subjecting the mixture obtained in (V), comprising the compound of formula (Ia), or the compound of formula (Ib), or the compound of formula (Ia) and the compound of formula (Ib), preferably comprising the compound of formula (Ia) and the compound of formula (Ib), to at least one repetition of the sequence of steps (III) to (V).

37. The process of embodiment 36, wherein according to (I), the composition is provided by a process according to any of embodiments 10 to 33.

38. The process of embodiment 36 or 37, wherein the hydrogenation catalyst according to (II) comprises palladium preferably supported on a support preferably comprising at least on element selected from the group consisting of aluminum, barium, calcium, cerium, zirconium, titanium and silicon, more preferably comprising at least one compound selected from the group consisting of aluminum oxide, barium sulfate, calcium carbonate, cerium(IV) oxide, silicon oxide and zirconium(IV) oxide.

39. The process of any of embodiments 36 or 38, wherein at least 1 weight-%, more preferably at least 5 weight-%, more preferably at least 10 weight-%, more preferably at least 20 weight-%, more preferably at least 30 weight-% of the mixture comprising hydrogen peroxide obtained according to (V) consist of hydrogen peroxide.

40. A mixture comprising hydrogen peroxide, obtainable or obtained by a process according to any of embodiments 36 to 39, preferably obtainable or obtained in step (V) of a process according to any of embodiments 36 to 39.

41. Use of the mixture according to embodiment 40 for the preparation of propylene oxide, a propylene glycol, a polyol, and/or a polyurethane.

42. A compound of formula (IIa-i)

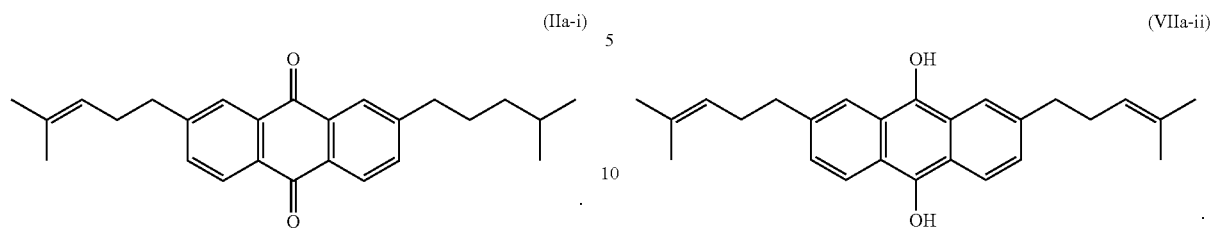
(IIa-i)

43. A compound of formula (IIb-i)

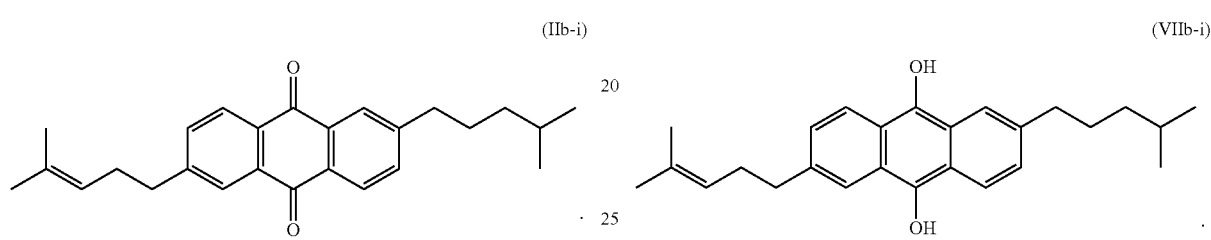
(IIb-i)

44. A mixture comprising a compound of formula (IIa-i)

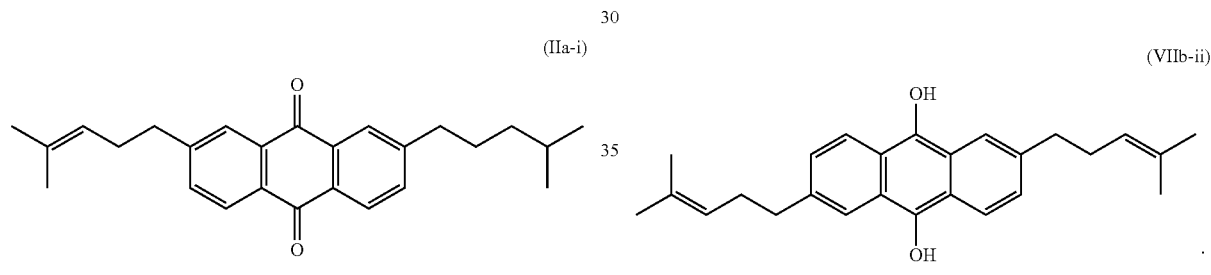
(IIa-i)

and/or, preferably and, a compound of formula (IIb-i)

(IIb-i)

45. A compound of formula (VIIa-i)

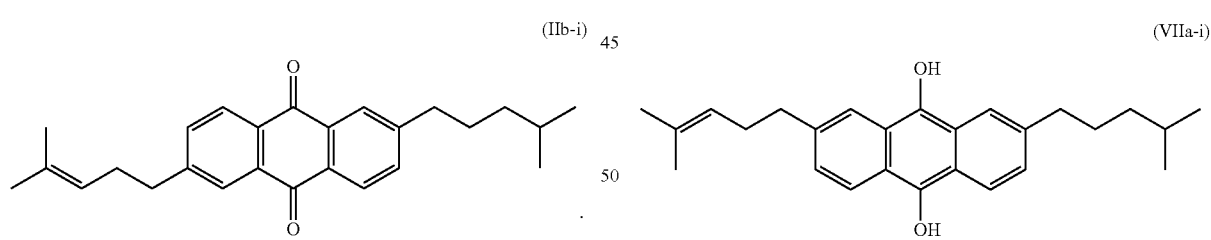
(VIIa-i)

46. A compound of formula (VIIa-ii)

(VIIa-ii)

47. A compound of formula (VIIb-i)

(VIIb-i)

48. A compound of formula (VIIb-ii)

(VIIb-ii)

49. A mixture comprising a compound of formula (VIIa-i)

(VIIa-i)

and/or, preferably and, a compound of formula (VIIb-i);

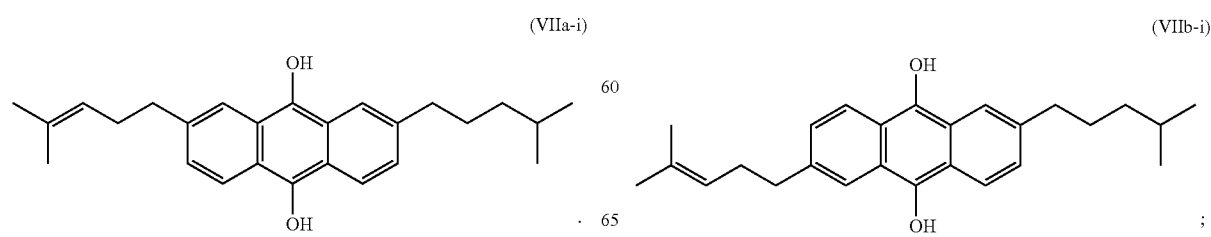
(VIIb-i)

and/or comprising a compound of formula (VIIa-ii)

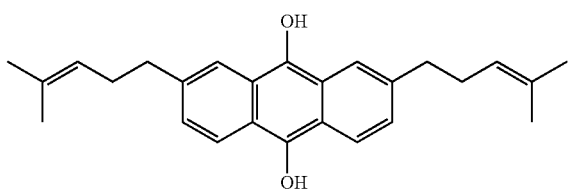
(VIIa-ii)

and/or, preferably and, a compound of formula (VIIb-ii)

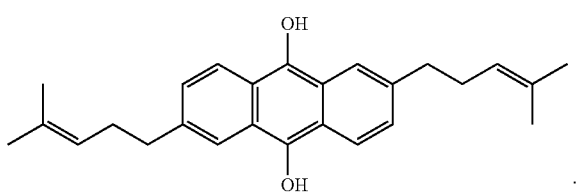
(VIIb-ii)

The present invention is further illustrated by the following reference examples, examples, and comparative examples.

EXAMPLES

Reference Example 1: IR Measurements

The IR measurements were performed on a Nicolet 6700 spectrometer. The materials were measured as film on a KBr window, wherein in case the materials were present as solid, the solid was solved in dichloromethane prior to applying on the KBr window. The samples were introduced into a high vacuum cell placed into the IR instrument. The spectra were recorded in the range of 4000 cm$^{-1}$ to 400 cm$^{-1}$ at a resolution of 4 cm$^{-1}$. The obtained spectra were represented by a plot having on the x axis the wavenumber (cm$^{-1}$) and on the y axis the absorbance (arbitrary units). For the quantitative determination of the peak heights and the ratio of the peak heights, a baseline correction was carried out.

Reference Example 2: Elemental Analysis

The elemental analysis regarding carbon and hydrogen were performed on an elemental analyzer of model vario Micro cube of the company Elementar, wherein oxygen was used for combustion, and wherein the content of carbon and hydrogen were detected via conductivity measurement.

The elemental analysis regarding oxygen was performed on an elemental analyzer of model EuroVector EA3000 of the firm HEKAtech, wherein soot was used for pyrolysis, and wherein the content of oxygen was detected via conductivity measurement.

The measurements were carried out according to the manufacturer's instructions.

Reference Example 3: GC/MS Measurements

The GC/MS measurements were performed on a gas chromatograph Agilent GC 6890 N using a detector Agilent 5975 MSD and a column Restek 13623.

The measurements were carried out according to the manufacturer's instructions.

Example 1: Preparation of a Mixture of 2,6-bis(4-methylpent-3-enyl)-1,4,4a,5,8,8a,9a,10a-octahydroanthracene-9-10-dione and 2,7-bis(4-methylpent-3-enyl)-1,4,4a,5,8,8a,9a,10a-octahydroanthracene-9-10-dione (Compounds of Formula (Va) and (Vb))

A round bottom flask was equipped with a reflux condenser and flushed with argon. Then, 20.0 g cyclohexa-2,5-diene-1,4-dione were provided in the round bottom flask and suspended in 200 ml toluene. The obtained suspension was heated to an internal temperature of 90° C. and 63.0 g 7-methyl-3-methylene-1,6-octadiene were added and the mixture was stirred for 7 days at 80° C. with a stirring rate of 400 r.p.m. (rounds per minute). Thereafter, the mixture was cooled to 22° C. and filtered. The solvent in the obtained solution was evaporated under reduced pressure, so that a solid was obtained. Boiling ethanol was then added until the solid was dissolved completely. The solution was cooled to 22° C. and then further cooled to −22° C. for 15 h. The obtained solid was filtered off from the mother liquor and washed with ethanol having a temperature of −22° C. until the solid was colorless. The obtained product was dried under reduced pressure. The solvent in the mother liquor was evaporated and the thus obtained solid was purified as described above.

59.0 g (84%) of the mixture of 2,6-bis(4-methylpent-3-enyl)-1,4,4a,5,8,8a,9a,10a-octahydro-anthracene-9-10-dione and 2,7-bis(4-methylpent-3-enyl)-1,4,4a,5,8,8a,9a,10a-octahydro-anthracene-9-10-dione were obtained. The obtained product had a melting point of 73.9° C. and 77° C. IR spectrum of the obtained product exhibits the following absorption bands with maximums at (KBr pellet): 428 cm$^{-1}$, 510 cm$^{-1}$, 555 cm$^{-1}$, 782 cm$^{-1}$, 835 cm$^{-1}$, 912 cm$^{-1}$, 934 cm$^{-1}$, 982 cm$^{-1}$, 1106 cm$^{-1}$, 1129 cm$^{-1}$, 1176 cm$^{-1}$, 122 cm$^{-1}$, 1244 cm$^{-1}$, 1280 cm$^{-1}$, 1375 cm$^{-1}$, 1443 cm$^{-1}$, 1706 cm$^{-1}$, 2855 cm$^{-1}$, 2917 cm$^{-1}$, 2966 cm$^{-1}$. Further, the following data were found by mass spectrometry (GC/MS) and elemental analysis (EA): GC/MS: $C_{26}H_{36}O_2$ calculated (m/z): 380.27; determined (GC/MS, (m/z)): 380; EA: $C_{26}H_{36}O_2$ calculated: C: 82.06 weight-%, H: 9.53 weight-%, O: 8.41 weight-%, determined: C: 81.9 weight-%, H: 9.6 weight-%, O: 8.3 weight-%.

Example 2: Preparation of a Mixture of 2,6-bis(4-methylpent-3-enyl)anthracene-9,10-dione and 2,7-bis(4-methylpent-3-enyl)anthracene-9,10-dione (Compounds of Formula (IIa) and (IIb))

10.0 g of the product obtained in Example 1 were dissolved in 200 ml of a mixture of toluene and n-butanol having a volume ratio of 3:1. The resulting solution was heated to an internal temperature of 60° C. and 1.5 g KOH were added. After KOH was solved in the solution, technical air containing 4 volume-% oxygen, was passed through the solution with a flow rate of 10 l/h for a period of 24 h and with a stirring rate of 750 r.p.m. The obtained solution was extracted with 50 ml distilled water for two times. The organic layer was separated and dried over $Na_2SO_4$. The solvent in the solution was evaporated under reduced pressure, so that a solid was obtained. Boiling ethanol was then added until the solid was dissolved completely. The solution was cooled to 22° C. and then further cooled to −22° C. for 15 h. The obtained solid was filtered off from the mother liquor and washed with ethanol having a temperature of −22° C. until the solid was colorless. The obtained product was dried under reduced pressure. The solvent in the mother liquor was evaporated and the thus obtained solid was purified as described above.

8.70 g (89%) of a mixture of 2,6-bis(4-methylpent-3-enyl) anthracene-9,10-dione and 2,7-bis(4-methylpent-3-enyl)anthracene-9,10-dione were obtained. The obtained product had a melting point of 69.8° C. and 77.9° C. IR spectrum of the obtained product exhibits the following absorption bands with maximums at (KBr pellet): 462 cm$^{-1}$, 550 cm$^{-1}$, 621 cm$^{-1}$, 666 cm$^{-1}$, 718 cm$^{-1}$, 743 cm$^{-1}$, 833 cm$^{-1}$, 848 cm$^{-1}$, 879 cm$^{-1}$, 932 cm$^{-1}$, 970 cm$^{-1}$, 1151 cm$^{-1}$, 1104 cm$^{-1}$, 1221 cm$^{-1}$, 1258 cm$^{-1}$, 1300 cm$^{-1}$, 1325 cm$^{-1}$, 1383 cm$^{-1}$, 1439 cm$^{-1}$, 1574 cm$^{-1}$, 1596 cm$^{-1}$, 1673 cm$^{-1}$, 2858 cm$^{-1}$, 2919 cm$^{-1}$, 2963 cm$^{-1}$, 3029 cm$^{-1}$, 3054 cm$^{-1}$, 3433 cm$^{-1}$. Further, the following data were found by mass spectrometry (GC/MS) and elemental analysis (EA): GC/MS: $C_{26}H_{28}O_2$ calculated (m/z): 372.21 determined (m/z)): 372; EA: $C_{26}H_{28}O_2$ calculated: C: 83.83 weight-%, H: 7.58 weight-%, O: 8.59 weight-% determined: C: 82.9 weight-%, H: 7.6 weight-%, O: 8.8 weight-%.

Example 3: Preparation of a Mixture of 2,6-diisohexylanthracene-9,10-dione and 2,7-diisohexylanthracene-9,10-dione (Compounds of Formula (Ia) and (Ib)) by Use of a Palladium Catalyst on Carbon A solution of 2.25 g of the product obtained in Example 2 dissolved in 150 ml ethanol was provided in an autoclave. 0.65 g of a palladium catalyst on carbon (5% Pd/C) were added. The autoclave was closed and flushed with 10 bar nitrogen for five times. The solution was cooled by air cooling having 20° C. and the solution was stirred with a stirring rate of 700 r.p.m. Thereafter, the pressure was set to 3.0 bar by introducing hydrogen gas. The pressure decreased within approximately 2 h to 1 bar and thereafter, the pressure was again set to 3 bar by introducing hydrogen gas. After approximately 5 h the pressure decreased to 1 bar and stirring was stopped. The pressure was set to atmosphere pressure and the autoclave was flushed with 10 bar nitrogen for two times. The palladium catalyst was filtered off and the solvent of the obtained solution was evaporated under reduced pressure, so that a solid was obtained. Boiling ethanol was then added until the solid was dissolved completely. The solution was cooled to 22° C. and then further cooled to −22° C. for 15 h. The obtained solid was filtered off from the mother liquor and dried under reduced pressure.

The solvent in the mother liquor was evaporated and the thus obtained solid was purified as described above.

1.61 g (72%) a mixture of 2,6-diisohexylanthracene-9,10-dione and 2,7-diisohexyl-anthracene-9,10-dione were obtained. The obtained product had a melting point of 79.1° C. The IR spectrum of the obtained product exhibits the following absorption bands with maximums at (KBr pellet): 413 cm$^{-1}$, 553 cm$^{-1}$, 615 cm$^{-1}$, 654 cm$^{-1}$, 720 cm$^{-1}$, 750 cm$^{-1}$, 848 cm$^{-1}$, 879 cm$^{-1}$, 917 cm$^{-1}$, 934 cm$^{-1}$, 983 cm$^{-1}$, 1144 cm$^{-1}$, 1169 cm$^{-1}$, 1211 cm$^{-1}$, 1297 cm$^{-1}$, 1308 cm$^{-1}$, 1328 cm$^{-1}$, 1365 cm$^{-1}$, 1383 cm$^{-1}$, 1459 cm$^{-1}$, 1470 cm$^{-1}$, 1596 cm$^{-1}$, 1673 cm$^{-1}$, 2867 cm$^{-1}$, 2926 cm$^{-1}$, 2951 cm$^{-1}$, 3066 cm$^{-1}$, 3477 cm$^{-1}$. Further, the following data were found by mass spectrometry (GC/MS) and elemental analysis (EA): GC/MS: $C_{26}H_{32}O_2$ calculated (m/z): 376.24; determined (m/z): 376; EA: $C_{26}H_{32}O_2$ calculated: C: 82.94, H: 8.57, O: 8.50 determined: C: 82.3, H: 8.6, O: 8.9.

Results of Examples 1 to 3

Examples 1 to 3 show that 2,6-diisohexylanthracene-9,10-dione and 2,7-diisohexyl-anthracene-9,10-dione are obtained by a process according to the present invention in an overall yield of 54%.

Example 4: Preparation of a Mixture of 2,6-diisohexylanthracene-9,10-dione and 2,7-diisohexylanthracene-9,10-dione (Compounds of Formula (Ia) and (Ib)) by Use of Different Catalysts and Solvents 200 mg of the mixture obtained in Example 3, catalyst (the amount used is given in Table 1 below) and 5 ml solvent (the solvent used is given in Table 1 below) were provided in an autoclave having a nominal volume of 80 ml. The pressure was set to 20.0 bar by introducing hydrogen gas and the reaction mixture was stirred for 15 h at 40° C. Thereafter, the catalyst was separated by filtration and the solvent was evaporated under reduced pressure.

TABLE 1

| Complex | Ligand | Additive | Solvent | Conversion (starting material) | Selectivity (to product) |
|---|---|---|---|---|---|
| 10 mol-% [Rh(COD)$_2$][BF$_4$]$^{(1)}$ | 10 mol-% DTBPP$^{(2)}$ | — | MeOH | 100% | 75% |
| 17 mol % [Ru(COD)Cl$_2$]$_n$$^{(1)}$ | 10 mol-% PCy$_3$$^{(3)}$ | 35 mol % BMIMCl$^{(4)}$ | THF | 100% | 60% |
| 1 mol-% 2% Pd/C | — | — | MeOH | 100% | 29% |
| 1 mol-% 2% Pd/C | — | — | toluene | 100% | 18% |

$^{(1)}$COD = 1,5-cyclooctadiene
$^{(2)}$DTBPP = 1,2-bis(di-tert-butyl-phosphinomethyl)benzene
$^{(3)}$PCy$_3$ = tricyclohexylphosphin
$^{(4)}$BMIMCl = 1-butyl-3-methylimidazolium chloride Results of Example 4

Example 4 shows that a variety of homogeneous and heterogeneous catalysts and solvents may be used to hydrogenate 2,6-bis(4-methylpent-3-enyl)anthracene-9,10-dione and 2,7-bis(4-methylpent-3-enyl)anthracene-9,10-dione even at an absolute hydrogen pressure of 20 bar.

Example 5: Preparation of a Mixture of 2,6-diisohexylanthracene-9,10-dione and 2,7-diisohexylanthracene-9,10-dione (Compounds of Formula (Ia) and (Ib)) and Subsequent Treatment with KOH 15 g of the mixture obtained in Example 3, 2.5 g of a palladium catalyst on carbon (5% Pd/C) and 200 ml ethanol were provided in an autoclave. The autoclave was closed and flushed with 1 bar nitrogen for three times. The pressure was set to 1.5 bar by introducing hydrogen gas and the reaction mixture was stirred for 140 h at 25° C. Thereafter, the catalyst was separated by filtration and the solvent was evaporated under reduced pressure. The resulting reaction mixture was analyzed by GC-MS. The conversion of the starting material was 100% and the selectivity to 2,6-diisohexylanthracene-9,10-dione and 2,7-diisohexylanthracene-9,10-dione was 81%, the rest being over-hydrogenated byproducts The resulting solution was heated to an internal temperature of 60° C. and 3.8 g KOH were added. After KOH was solved in the solution, technical air containing 4 volume-% oxygen, was passed through the solution with a flow rate of 10 l/h for a period of 4 h and with a stirring rate of 750 r.p.m. The obtained solution was extracted with 70 ml distilled water for two times. The organic layer was separated and dried over $Na_2SO_4$. The solvent in the solution was evaporated under reduced pressure, so that a solid was obtained. Boiling ethanol was then added until the solid was dissolved completely. The solution was cooled to 22° C. and then further cooled to −22° C. for 15 h. The obtained solid was filtered off from the mother liquor and washed with ethanol having a temperature of −22° C. until the solid was colorless. The obtained product was dried under reduced pressure. The solvent in the mother liquor was evaporated and the thus obtained solid was purified as described above.

The resulting reaction mixture was analyzed by GC-MS, wherein the selectivity to 2,6-diisohexylanthracene-9,10-dione and 2,7-diisohexylanthracene-9,10-dione was 97%.

Results of Example 5

Example 5 shows that a subsequent treatment with potassium hydroxide leads to an increased selectivity to 2,6-diisohexylanthracene-9,10-dione and 2,7-diisohexylanthracene-9,10-dione. Without the treatment with potassium hydroxide, a selectivity to 2,6-diisohexylanthracene-9,10-dione and 2,7-diisohexylanthracene-9,10-dione of 81% is achieved, wherein the subsequent treatment with potassium hydroxide increases the selectivity to 97%. This can be explained by the re-oxidation of the over-hydrogenated byproducts that are generated in the hydrogenation step even under such mild conditions described.

Example 6: Preparation of a Mixture of 2,6-bis(4-methylpent-3-enyl)anthracene-9,10-dione and 2,7-bis(4-methylpent-3-enyl)anthracene-9,10-dione (Compounds of Formula (IIa) and (IIb)) Starting from 1,4-dihydroxybenzol (Compound of Formula (VI))

0.19 g copper chloride dihydrate and 0.19 g dry lithium chloride were dissolved in 8 ml distilled water in a round bottom flask, which was equipped with a reflux condensor. 17 ml n-hexanol were added and the obtained solution was heated to an internal temperature of 60° C. 1.55 g 7-methyl-3-methylene-1,6-octadiene and 0.5 g 1,4-dihydroxybenzol were added. Thereafter, technical air was passed through the solution for 96 h, wherein the solution was stirred with a stirring rate of 900 r.p.m. Then, the organic layer was separated, heated to 70° C. and 0.25 g potassium hydroxide were added. Technical air was passed through the thus obtained mixture for 10 h. Thereafter, the obtained mixture was extracted with 30 ml distilled water and dried over $Na_2SO_4$. The solvent in the solution was evaporated under reduced pressure, so that a solid was obtained. Boiling ethanol was then added until the solid was dissolved completely. The solution was cooled to 22° C. and then further cooled to −22° C. for 15 h. The obtained solid was filtered off from the mother liquor and dried under reduced pressure, wherein a selectivity to 2,6-bis(4-methylpent-3-enyl)anthracene-9,10-dione and 2,7-bis(4-methylpent-3-enyl)anthracene-9,10-dione of 69% was achieved.

Results of Example 6

Example 6 shows that 2,6-bis(4-methylpent-3-enyl)anthracene-9,10-dione and 2,7-bis(4-methylpent-3-enyl)anthracene-9,10-dione may be obtained in a one-pot process starting from 1,4-dihydroxybenzene, wherein a combination of copper chloride and lithium chloride is used as catalyst.

Example 7: Preparation of a Mixture of 2,6-bis(4-methylpent-3-enyl)-1,4,4a,5,8,8a,9a,10a-octahydroanthracene-9-10-dione and 2,7-bis(4-methylpent-3-enyl)-1,4,4a,5,8,8a,9a,10a-octahydroanthracene-9-10-dione (Compounds of Formula (IIa) and (IIb)) Starting from 1,4-dihydroxybenzene (Compound of Formula (VI))

0.49 g of a catalyst consisting of 60 weight-% copper(II) oxide, 20 weight-% zinc(II) oxide, 17.5 weight-% aluminum (III) oxide, 2.5 weight-% zirconium (IV) oxide were suspended in a mixture of 15 mL distilled water and 30 mL of 2-ethylhexanol. The obtained suspension was heated to an internal temperature of 60° C. and 4.65 g 7-methyl-3-methylene-1,6-octadiene and 1.5 g 1,4-dihydroxybenzol were added to the suspension. Thereafter, technical air was passed through the solution for 72 h, wherein the solution was stirred. The resulting reaction mixture was cooled to 22° C. and the organic layer was separated, dried over $Na_2SO_4$ and the solvent was evaporated under reduced pressure. The obtained solid was recrystallized in ethanol, wherein 5.18 g (yield: 84%) of 2,6-bis(4-methylpent-3-enyl)-1,4,4a,5,8,8a,9a,10a-octahydroanthracene-9-10-dione and 2,7-bis(4-methyl-pent-3-enyl)-1,4,4a,5,8,8a,9a,10a-octahydroanthracene-9-10-dione were obtained. The product obtained was further treated with KOH in the presence of an oxygen containing gas according to Example 2 to obtain 2,6-bis(4-methylpent-3-enyl)anthracene-9,10-dione and 2,6-bis(4-methylpent-3-enyl)anthracene-9,10-dione.

Results of Example 7

Example 7 shows that 2,6-bis(4-methylpent-3-enyl)-1,4,4a,5,8,8a,9a,10a-octahydroanthracene-9-10-dione and 2,7-bis(4-methylpent-3-enyl)-1,4,4a,5,8,8a,9a,10a-octahydroanthracene-9-10-dione and further 2,6-bis(4-methylpent-3-enyl)anthracene-9,10-dione and later on 2,7-bis(4-methylpent-3-enyl)anthracene-9,10-dione may be obtained by use of different catalyst and solvents, where in 2-ethylhexanol and an heterogeneous catalyst containing copper, zinc, aluminum and zirconium is used.

Example 8: Preparation of a Mixture of 2,6-bis(4-methylpent-3-enyl)anthracene-9,10-dione and 2,7-bis(4-methylpent-3-enyl)anthracene-9,10-dione starting (Compounds of Formula (Va) and (Vb)) from 1,4-dihydroxybenzene (Compound of Formula (VI))

0.49 g of a catalyst consisting of 60 weight-% copper(II) oxide, 20 weight-% zinc(II) oxide, 17.5 weight-% aluminum (III) oxide, 2.5 weight-% zirconium (IV) oxide were suspended in a mixture of 15 mL distilled water and 30 mL of 2-ethylhexanol. The obtained suspension was heated to an internal temperature of 60° C. 4.65 g 7-methyl-3-methylene-1,6-octadiene and 1.5 g 1,4-dihydroxybenzol were added to the suspension. Thereafter, technical air was passed through the solution for 240 h, wherein the solution was stirred. The resulting reaction mixture was cooled to 22° C. and the organic layer was separated, dried over $Na_2SO_4$ and the solvent was evaporated under reduced pressure. The obtained solid was recrystallized in ethanol, wherein 4.51 g of 2,6-bis(4-methylpent-3-enyl)anthracene-9,10-dione and 2,7-bis(4-methylpent-3-enyl)anthracene-9,10-dione starting from benzene-1,4-diol were obtained.

Results of Example 7 and 8

Comparison of Example 7 with Example 8 shows that an extension of the reaction time leads to an oxidation of 2,6-bis(4-methylpent-3-enyl)-1,4,4a,5,8,8a,9a,10a-octahydro-anthracene-9-10-dione and 2,7-bis(4-methylpent-3-enyl)-1,4,4a,5,8,8a,9a,10a-octahydroanthracene-9-10-dione by the technical air used, wherein 2,6-bis(4-methylpent-3-enyl)anthracene-9,10-dione and 2,7-bis(4-methylpent-3-enyl)anthracene-9,10-dione starting from benzene-1,4-diol are obtained without the use of a catalyst.

Comparative Example 1: Preparation of a Mixture of 2,6-bis(4,8-dimethylnonane-3,7-dienyl)-1,4,4a,5,8,8a,9a,10a-octahydroanthracene-9-10-dione and 2,7-bis(4,8-dimethylnonane-3,7-dienyl)-1,4,4a,5,8,8a,9a,10a-octahydroanthracene-9-10-dione A round bottom flask was equipped with a reflux condenser and flushed with argon. Then, 2.0 g cyclohexa-2,5-diene-1,4-dione were provided in the round bottom flask and suspended in 20 ml toluene. The obtained suspension was heated to an internal temperature of 80° C. and 9.0 g (6E)-7,11-dimethyl-3-methylene-1,6,10-dodecatrien were added and the mixture was stirred for 14 days at 80° C. with a stirring rate of 700 r.p.m. Thereafter, the mixture was cooled to 22° C. and filtered. The solvent in the obtained solution was evaporated under reduced pressure, so that a solid was obtained. The resulting crude product was purified by chromatography on silica using cyclohexane and ethyl acetate (volume ratio 40:1) as eluent.

6.71 g (61%) of 2,6-bis(4,8-dimethylnonane-3,7-dienyl)-1,4,4a,5,8,8a,9a,10a-octahydro-anthracene-9-10-dione and 2,7-bis(4,8-dimethylnonane-3,7-dienyl)-1,4,4a,5,8,8a,9a,10a-octahydroanthracene-9-10-dione in form of an oil were obtained. IR spectrum of the obtained product exhibits the following absorption bands with maximums at (KBr pellet): 432 $cm^{-1}$, 451 $cm^{-1}$, 551 $cm^{-1}$, 594 $cm^{-1}$, 826 $cm^{-1}$, 886 $cm^{-1}$, 921 $cm^{-1}$, 984 $cm^{-1}$, 1041 $cm^{-1}$, 1159 $cm^{-1}$, 1108 $cm^{-1}$, 1215 $cm^{-1}$, 1282 $cm^{-1}$, 1376 $cm^{-1}$, 1440 $cm^{-1}$, 1601 $cm^{-1}$, 1674 $cm^{-1}$, 1713 $cm^{-1}$, 2729 $cm^{-1}$, 2850 $cm^{-1}$, 2918 $cm^{-1}$, 2966 $cm^{-1}$, 3413 $cm^{-1}$. Further, the following data were found by mass spectrometry (GC/MS): $C_{36}H_{52}O_2$ calculated (m/z): 516.40 determined (m/z): 516.

Comparative Example 2: Preparation of a Mixture of 2,6-bis(4,8-dimethylnonan-3,7-dienyl)anthracene-9,10-dione and 2,7-bis(4,8-dimethylnonan-3,7-dienyl)anthracene-9,10-dione 4.0 g of the product obtained in Comparative Example 1 were dissolved in 74.5 ml of a mixture of toluene and n-butanol having a volume ratio of 3:1. The resulting solution was heated to an internal temperature of 60° C. and 0.434 g KOH were added. After KOH was solved in the solution, compressed air was passed through the solution with a stirring rate of 700 r.p.m. The obtained solution was extracted with 30 ml distilled water for two times. The organic layer was separated and dried over $Na_2SO_4$. The solvent in the solution was evaporated under reduced pressure, so that a solid was obtained. Boiling ethanol was then added until the solid was dissolved completely. The solution was cooled to 22° C. and then further cooled to −22° C. for 15 h. The obtained solid was filtered off from the mother liquor and washed with ethanol having a temperature of −22° C. until the solid was colorless. The obtained product was dried under reduced pressure. The solvent in the mother liquor was evaporated and the thus obtained solid was purified by chromatography on silica using cyclohexane and ethyl acetate (volume ratio 40:1) as eluent.

3.60 g (yield: 90%) of 2,6-bis(4,8-dimethylnonan-3,7-dienyl)anthracene-9,10-dione in form of a crystalline solid and 1.11 g 2,7-bis(4,8-dimethylnonan-3,7-dienyl)anthracene-9,10-dione in form of an oil were obtained. 2,6-bis(4,8-dimethylnonan-3,7-dienyl)anthracene-9,10-dione had a melting point of 82.4° C. IR spectrum of the obtained product exhibits the following absorption bands with maximums at (KBr pellet): 414 $cm^{-1}$, 452 $cm^{-1}$, 596 $cm^{-1}$, 618 $cm^{-1}$, 653 $cm^{-1}$, 718 $cm^{-1}$, 726 $cm^{-1}$, 750 $cm^{-1}$, 807 $cm^{-1}$, 881 $cm^{-1}$, 852 $cm^{-1}$, 918 $cm^{-1}$, 973 $cm^{-1}$, 1110 $cm^{-1}$, 1147 $cm^{-1}$, 1212 $cm^{-1}$, 1262 $cm^{-1}$, 1298 $cm^{-1}$, 1324 $cm^{-1}$, 1383 $cm^{-1}$, 1451 $cm^{-1}$, 1594 $cm^{-1}$, 1670 $cm^{-1}$, 2853 $cm^{-1}$, 2913 $cm^{-1}$, 2968 $cm^{-1}$, 3442 $cm^{-1}$. Further, the following data were found by mass spectrometry (GC/MS) and elemental analysis (EA): GC/MS: $C_{36}H_{44}O_2$ calculated (m/z): 508.33, determined (m/z): 508; EA of 2,6-bis(4,8-dimethylnonan-3,7-dienyl)anthracene-9,10-dione $C_{36}H_{44}O_2$ calculated: C: 84.99 weight-%, H: 8.72 weight-%, O: 6.29 weight-%; determined: C: 83.1 weight-%, H: 8.6 weight-%, O: 7.8 weight-%.

Comparative Example 3: Preparation of a Mixture of 2,6-(1,5-dimethyl)-nonylanthracene-9,10-dione and 2,7-(1,5-dimethyl)-nonylanthracene-9,10-dione 3.0 g of the mixture obtained in Comparative Example 2, 0.32 g Rh(COD)$_2$BF$_4$ and 100 ml Methanol were provided in an autoclave having a nominal volume of 300 ml. The pressure was set to 20.0 bar by introducing hydrogen gas and the reaction mixture was stirred for 48 h at 40° C. Thereafter, the catalyst was separated by filtration and the solvent was evaporated under reduced pressure.

2.1 g (70%) of a mixture of 2,6-diisohexylanthracene-9,10-dione and 2,7-diisohexyl-anthracene-9,10-dione were obtained in form of a wax. IR spectrum of the obtained mixture exhibits the following absorption bands with maximums at (KBr pellet): 415 $cm^{-1}$, 556 $cm^{-1}$, 623 $cm^{-1}$, 655 $cm^{-1}$, 751 $cm^{-1}$, 879 $cm^{-1}$, 934 $cm^{-1}$, 983 $cm^{-1}$, 1146 $cm^{-1}$, 1171 $cm^{-1}$, 1211 $cm^{-1}$, 1308 $cm^{-1}$, 1328 $cm^{-1}$, 1365 $cm^{-1}$, 1459 cm$^{-1}$, 1470 cm$^{-1}$, 1675 cm$^{-1}$, 2867 cm$^{-1}$, 2951 cm$^{-1}$, 3066 cm$^{-1}$, 3469 cm$^{-1}$. Further, the following data were found by mass spectrometry (GC/MS) and elemental analysis (EA): GC/MS: $C_{26}H_{32}O_2$ calculated (m/z): 516.40; determined (m/z): 516; EA: $C_{26}H_{32}O_2$ calculated: C: 83.67 weight-%, H: 10.14 weight-%, O: 6.19 weight-%; determined: C: 83.75 weight-%, H: 10.22 weight-%, O: 6.03 weight-%.

Comparative Example 4: Preparation of 2-(3-methylbut-2-en-1-yl)-anthracene-9,10-dione 2-(3-methylbut-2-en-1-yl-anthracene-9,10-dione was prepared according to Example 8 in EP 1 178 032 A1: 850 g naphthoquinone were added to a mixture of 4 l toluene and 1.3 l n-butane and the obtained mixture was heated to 90° C. Thereafter, 990 g myrcene were added and after 5 h the mixture was cooled to 70° C. 250 ml water, 52 ml 50% NaOH and 50 ml diethyl amine were added and the resulting mixture was purged by oxygen gas at 70° C. for a period of 5 h. The aqueous layer was separated and the organic layer was washed with diluted phosphoric acid. The solvent in the organic layer was evaporated under reduced pressure and the crude product was purified by crystallization.

Comparative Example 5: Preparation of 2,3,6,7-tetramethyl-1,4,4a,5,8,8a,9a,10a-octahydroanthracene-9,10-dione 10.0 g cyclohexa-2,5-diene-1,4-dione were suspended in 30 ml of a mixture of toluene and n-butanol having a volume ratio of 3:1. This suspension and 10.26 g 2,3-dimethylbuta-1,3-diene were provided in an autoclave having a nominal volume of 100 ml and the obtained mixture was heated to an internal temperature of 90° C. and stirred for 2 days at this temperature. Thereafter, the mixture was cooled to 22° C. and filtered. The thus obtained solution was used for the preparation of 2,3,6,7-tetramethylanthracene-9,10-dione without further purification.

Comparative Example 6: Preparation of 2,3,6,7-tetramethylanthracene-9,10-dione

The solution obtained in Comparative Example 5 was set to a temperature of 60° C. and then 5.13 g KOH were added. After KOH was dissolved completely, compressed air was passed through the solution for a period of 5 h with a stirring rate of 700 r.p.m. Thereafter, the mixture was cooled to 22° C. and the solid thus created was separated by filtration and washed with cooled dichloromethane and water. The obtained solid was dried for 24 h at 70° C. in vacuum. The IR spectrum of the obtained mixture exhibits the following absorption bands with maximums at (KBr pellet): 412 cm$^{-1}$, 542 cm$^{-1}$, 655 cm$^{-1}$, 743 cm$^{-1}$, 872 cm$^{-1}$, 934 cm$^{-1}$, 1146 cm$^{-1}$, 1170 cm$^{-1}$, 1211 cm$^{-1}$, 1308 cm$^{-1}$, 1328 cm$^{-1}$, 1365 cm$^{-1}$, 1459 cm$^{-1}$, 1470 cm$^{-1}$, 1684 cm$^{-1}$, 2867 cm$^{-1}$, 3123 cm$^{-1}$, 3415 cm$^{-1}$. Further, the following data were found by mass spectrometry (GC/MS) and elemental analysis (EA): GC/MS: $C_{18}H_{16}O_2$ calculated (m/z): 264.12; determined (m/z): 264; EA: $C_{18}H_{16}O_2$ calculated: C: 81.79 weight-%, H: 6.10 weight-%, O: 12.11 weight-%; determined: C: 81.53 weight-%, H: 6.05 weight-%, O: 12.42 weight-%.

Example 9: Determination of the Solubility 0.06 ml of a mixture of xylene (50 volume-%) and diisobutylcarbinol (50 volume-%) were added to 1 g of the respective anthraquinone derivative at 22° C. every 60 seconds until the anthraquinone derivative was dissolved completely. The results of the solubility test are shown in Table 2 below.

TABLE 2

| Obtained from | Anthraquinone derivative | Solubility [mol/l] |
|---|---|---|
| Example 2 | 2,7-bis(4-methylpent-3-enyl)anthracene-9,10-dione and 2,6-bis(4-methylpent-3-enyl)anthracene-9,10-dione | 0.77 |
| Example 3 | 2,7-diisohexylanthracene-9,10-dione and 2,6-diisohexylanthracene-9,10-dione | 1.61 |
| Comparative Example 2 | 2,6-bis(4,8-dimethylnonan-3,7-dienyl)anthracene-9,10-dione and 2,7-bis(4,8-dimethylnonan-3,7-dienyl)anthracene-9,10-dione | 0.65 |
| Comparative Example 3 | 2,6-(1,5-dimethy)-nonylanthracene-9,10-dione and 2,7-(1,5-dimethy)-nonylanthracene-9,10-dione | 0.39 |
| Comparative Example 4 | 2-(3-methylbut-2-en-1-yl)-anthracene-9,10-dione | 0.77 |
| Comparative Example 6 | 2,3,6,7-tetramethylanthracene-9,10-dione | insoluble |
| (commercially available) | 2-ethylanthraquinone | 0.27 |

Results of Example 9

As may be taken from the solubility test of the different anthraquinone derivatives, the anthraquinone derivatives having small substituents are insoluble (anthraquinone derivative obtained from Comparative Example 6) or only poorly soluble (commercially available anthraquinone derivative) in the used solvent system compared to the anthraquinone derivatives having 2 substituents, wherein these substituents have six or eleven carbon atoms. However, the anthraquinone derivative according to the present invention, which is obtained from Example 3 exhibits the highest solubility in the solvent system used.

Example 10: Preparation of Hydrogen Peroxide by Use of Anthraquinone Derivatives 5 g of the anthraquinone derivative obtained from Example 3 was dissolved in an equivolume mixture of xylene and diisobutylcarbinol at 30° C. to obtain 100 ml of an anthraquinone solution. 2 g of a palladium catalyst on alumina was added to 50 ml of the anthraquinone solution and then the solution was made to absorb the theoretical amount of hydrogen at 30° C. The obtained solution has been left untouched for 15 h to thoroughly precipitate the excess of anthrahydroquinone. After the catalyst and the precipitate have been separated by filtration under a current of nitrogen, the resulting solution was stirred under air in order to oxidize the anthrahydroquinone back to the corresponding anthraquinone. The produced hydrogen peroxide was extracted with water. After the extraction of the hydrogen peroxide was completed, 25 mL of the working solution were further submitted to subsequent hydrogenation at 30° C. as described above until a state of saturation was reached. The amount of absorbed hydrogen until the precipitation of the anthrahydroquinone that was observed corresponded to a solubility of the anthrahydroquinone obtained from the anthraquinone described in Example 3 in said equivolume mixture of xylene and diisobutylcarbinol of 1.01 mol/l.

Results of Example 10

TABLE 3

| Alkylanthrahydro-quinone obtained from | Anthraquinone derivative | Solubility [mol/l] | Yield of hydrogen peroxide [g/l] |
|---|---|---|---|
| Example 3 | 2,7-diisohexylanthracene-9,10-dione and 2,6-diisohexylanthracene-9,10-dione (Ia and Ib) | 1.01 | 32.4 |

Summary of the Examples

As shown in Examples 1 to 8, 2,6-diisohexylanthracene-9,10-dione and 2,7-diisohexyl-anthracene-9,10-dione may be obtained by a sustainable and atom efficient process according to the present invention. Further, Example 9 shows 2,6-diisohexylanthracene-9,10-dione and 2,7-diisohexylanthracene-9,10-dione according to the present invention exhibit the advantage that these compound have the highest solubility in the solvent system used when compared to the anthraquinone derivatives obtained according to the Comparative Examples.

CITED LITERATURE

Ullmann's Encyclopedia of Industrial Chemistry, Vol. 18, chapter "Hydrogen Peroxide", DOI: 10.1002/14356007.a13_443.pub2.
GB 1 387 511 A1
GB 1 387 512
DE 43 39 649 A1
DE 1 051 257

The invention claimed is:

1. A compound of formula (Ia)

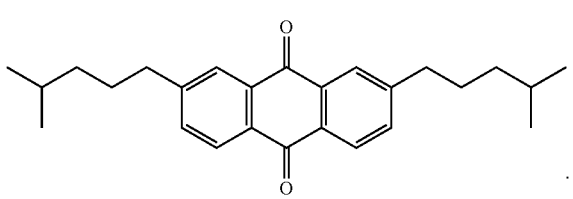

(Ia)

2. A compound of formula (Ib)

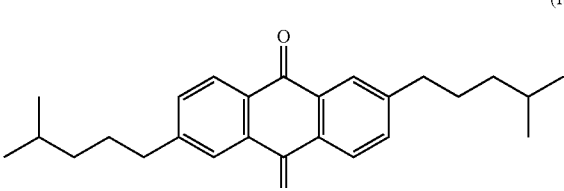

(Ib)

3. A composition, comprising a compound of formula (Ia)

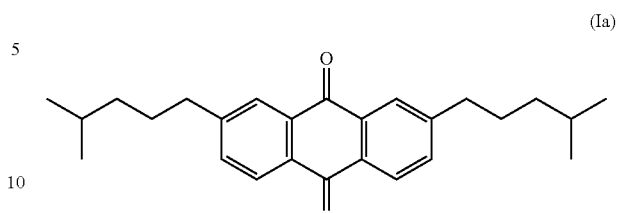

(Ia)

and a compound of formula (Ib)

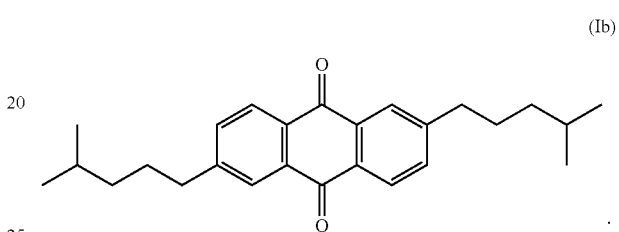

(Ib)

4. The composition of claim 3, wherein at least 90 weight-% of the composition consists of the compounds of formula (Ia) and formula (Ib).

5. The composition of claim 3, wherein the molar ratio of the compound of formula (Ia) relative to the compound of formula (Ib) is in a range of from 0.2:1 to 5:1.

6. The composition of claim 3, having a solubility of at least 1.0 mol/l in a solvent mixture of which at least 99.9 weight-% consists of ortho-xylene and diisobutyl carbinol wherein the molar ratio of the ortho-xylene relative to the diisobutyl carbinol in a range of from 0.99:1 to 1.01:1, wherein said solubility refers to the molar amount of the compound of formula (Ia) plus the molar amount of the compound of formula (Ib) dissolved in 1 l of the solvent mixture at a temperature of from 20 to 23° C. and at a pressure of from 0.9 to 1.1 bar.

7. The composition of claim 3, wherein at least 90 weight-% of the compound of formula (Ia) and at least 96 weight-% of the compound of formula (Ib) are present in solid form.

8. The composition of claim 3, being at least partially dissolved in a solvent.

9. A solution, comprising a compound of formula (Ia)

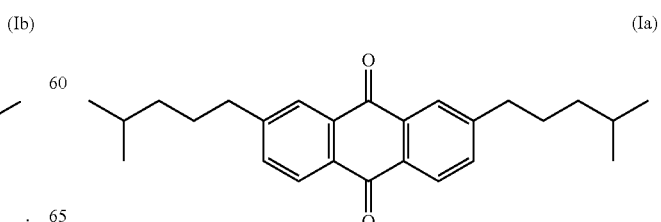

(Ia)

and/or a compound of formula (Ib)

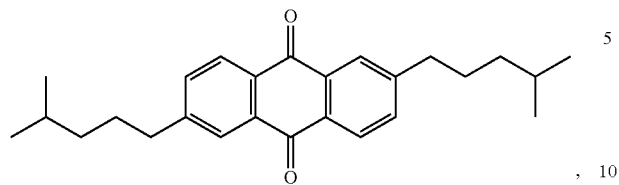
(Ib)

and a solvent.

10. A process for preparing a composition comprising a compound of formula (Ia)

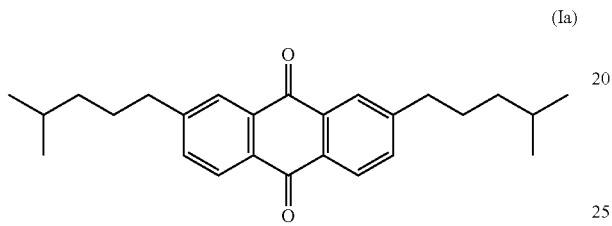
(Ia)

and a compound of formula (Ib)

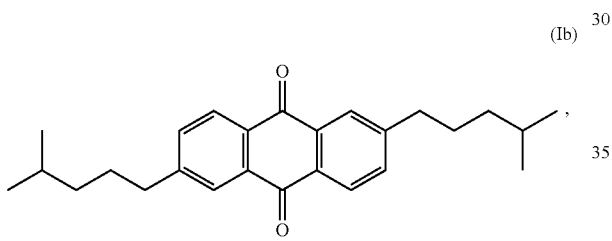
(Ib)

said process comprising:
(i) providing a mixture comprising the compound of formula (IIa)

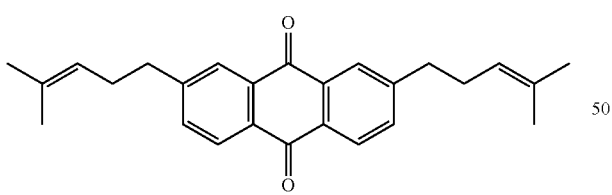
(IIa)

and the compound of formula (IIb)

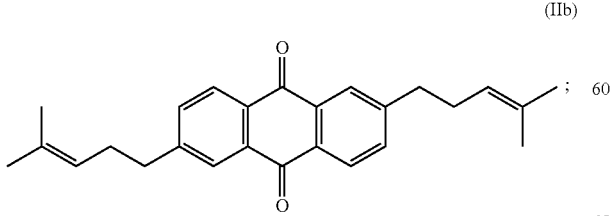
(IIb)

and
(ii) subjecting the mixture to a hydrogenation reaction.

11. The process of claim 10, wherein (i) comprises
(a) providing a compound of formula (III)

(III)

(b) reacting the compound of formula (III) with a compound of formula (IV)

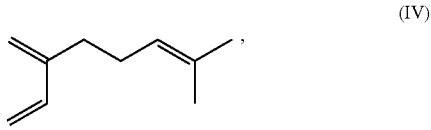
(IV)

thereby obtaining a mixture comprising a compound of formula (Va)

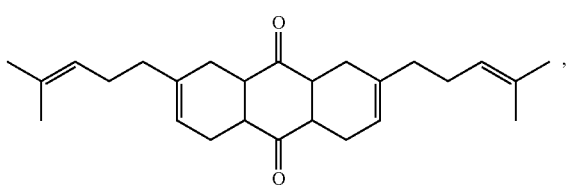
(Va)

and a compound of formula (Vb)

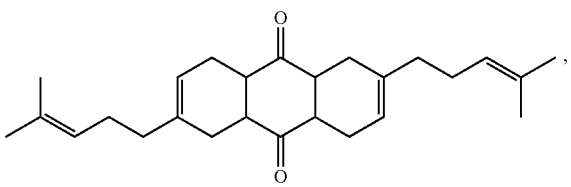
(Vb)

and
(c) subjecting the mixture obtained in (b) to an oxidation reaction thereby obtaining a mixture comprising the compound of formula (IIa) and the compound of formula (IIb).

12. The process of claim 11, wherein the reacting (b) is carried out in a solvent.

13. The process of claim 11, further comprising: after (b) and prior to (c),
(b') separating the compounds of formula (Va) and formula (Vb) from the mixture obtained in (b), thereby obtaining a mixture comprising the compounds of formula (Va) and formula (Vb).

14. The process of claim 11, wherein prior to (c), the compounds of formula (Va) and formula (Vb) are not separated from the mixture obtained in (b).

15. The process of claim 11, wherein the oxidation reaction in (c) is carried out in a solvent.

16. The process of claim 11, further comprising: after (c) and prior to (ii),
(c') separating the compounds of formula (IIa) and formula (IIb) from the mixture obtained in (c), thereby obtaining a mixture comprising the compounds of formula (IIa) and formula (IIb).

17. The process of claim 11, wherein after (c) and prior to (ii), the compounds of formula (IIa) and formula (II) are not separated from the mixture obtained in (c).

18. The process of claim 10, wherein the hydrogenation reaction in (ii) is carried out in a solvent in the presence of a hydrogenation catalyst.

19. The process of claim 10, further comprising
(iii) treating the mixture obtained in (ii) with an inorganic base, thereby obtaining a mixture comprising the compounds of formula (Ia) and formula (Ib).

20. The process of claim 10, further comprising crystallizing the compounds of formula (Ia) and formula (Ib) from the mixture obtained in (ii).

21. A mixture or a composition, comprising the compounds of formula (Ia)

(Ia)

and of formula (Ib)

(Ib)

obtained by the process of claim 10.

22. A process for preparing hydrogen peroxide, the process comprising:
preparing hydrogen peroxide from a compound selected from the group consisting of a compound of formula (Ia), a compound of formula (Ib), and a combination thereof:

(Ia)

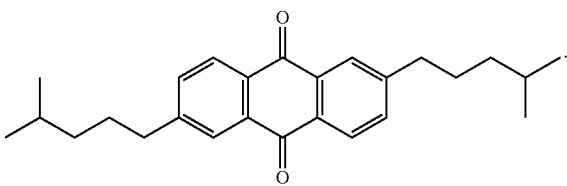

(Ib)

23. A process for preparing hydrogen peroxide, the process comprising
(I) providing a compound of formula (Ia)

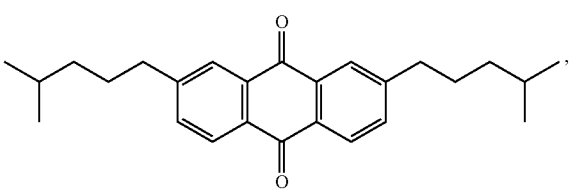

(Ia)

or a compound of formula (Ib)

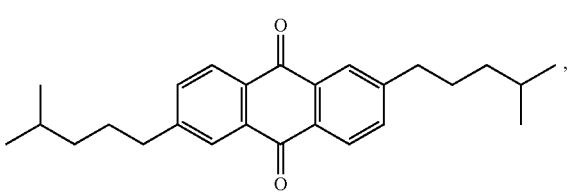

(Ib)

or a composition comprising the compound of formula (Ia) and the compound of formula (Ib);

(II) preparing a mixture comprising the compound or the composition provided in (I) dissolved in an organic solvent, and further comprising a hydrogenation catalyst;

(III) subjecting the mixture prepared in (II) to a hydrogenation reaction, thereby obtaining a mixture comprising a compound of formula (VIIa)

(VIIa)

or comprising a compound of formula (VIIb)

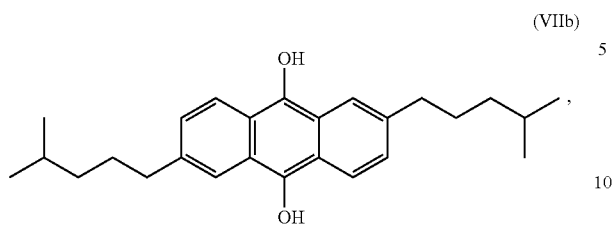

or comprising the compound of formula (VIIa) and the compound formula (VIIb);
(IV) subjecting the mixture obtained in (III) to an oxidation reaction in the presence of an oxygen containing gas, thereby obtaining a mixture comprising the compound of formula (Ia), or the compound of formula (Ib), or the compound of formula (Ia) and the compound of formula (Ib), and further comprising hydrogen peroxide; and
(V) separating hydrogen peroxide from the mixture obtained in (IV), thereby obtaining a mixture comprising hydrogen peroxide and a mixture comprising the compound of formula (Ia), or the compound of formula (Ib), or the compound of formula (Ia) and the compound of formula (Ib).

* * * * *

UNITED STATES PATENT AND TRADEMARK OFFICE
CERTIFICATE OF CORRECTION

| | | |
|---|---|---|
| PATENT NO. | : 9,988,268 B2 | Page 1 of 1 |
| APPLICATION NO. | : 15/314560 | |
| DATED | : June 5, 2018 | |
| INVENTOR(S) | : Dominic Riedel et al. | |

It is certified that error appears in the above-identified patent and that said Letters Patent is hereby corrected as shown below:

In the Specification

In Column 4, Line 27, after "esters" insert -- . --.

In Column 5, Line 15, delete "tetramethylbenzene" insert -- tetramethylbenzene, --, therefor.

In Column 16, Line 4, delete "tricyclohexylphosphin" insert -- tricyclohexylphosphine --, therefor.

In Column 16, Lines 9-10, delete "tricyclohexylphosphin" insert -- tricyclohexylphosphine --, therefor.

In Column 32, Line 28, after "72 h" insert -- . --.

In Columns 41-42, Line 55 (approx.), delete "tricyclohexylphosphin" insert -- tricyclohexylphosphine --, therefor.

In Column 43, Line 63, delete "condensor." insert -- condenser. --, therefor.

In Column 45, Line 58, delete "octahydro-anthracene" insert -- octa-hydronathracene --, therefor.

In Column 48, Line 18, delete "dimethy)" insert -- dimethyl) --, therefor,

In Column 48, Line 20, delete "dimethy)" insert -- dimethyl) --, therefor.

Signed and Sealed this
Tenth Day of September, 2019

Andrei Iancu
*Director of the United States Patent and Trademark Office*